US012622979B2

(12) United States Patent
Tange et al.

(10) Patent No.: US 12,622,979 B2
(45) Date of Patent: May 12, 2026

(54) LIPID NANOPARTICLE USED FOR DELIVERING NUCLEIC ACID TO BRAIN TISSUE

(71) Applicants: NOF CORPORATION, Tokyo (JP); NATIONAL UNIVERSITY CORPORATION CHIBA UNIVERSITY, Chiba (JP)

(72) Inventors: Kota Tange, Kawasaki (JP); Hiroki Yoshioka, Kawasaki (JP);

(Continued)

(73) Assignees: NOF CORPORATION, Tokyo (JP); NATIONAL UNIVERSITY CORPORATION CHIBA UNIVERSITY, Chiba (JP)

( * ) Notice: Subject to any disclaimer, the term of this patent is extended or adjusted under 35 U.S.C. 154(b) by 160 days.

(21) Appl. No.: 18/697,213

(22) PCT Filed: Sep. 26, 2022

(86) PCT No.: PCT/JP2022/035636

§ 371 (c)(1),
(2) Date: Mar. 29, 2024

(87) PCT Pub. No.: WO2023/054241

PCT Pub. Date: Apr. 6, 2023

(65) Prior Publication Data

US 2024/0408230 A1 Dec. 12, 2024

(30) Foreign Application Priority Data

Sep. 30, 2021 (JP) ................................ 2021-161237

(51) Int. Cl.
*A61K 48/00* (2006.01)
*A61K 9/51* (2006.01)

(52) U.S. Cl.
CPC ........ *A61K 48/0033* (2013.01); *A61K 9/5123* (2013.01)

(58) Field of Classification Search
None
See application file for complete search history.

(56) References Cited

U.S. PATENT DOCUMENTS

2014/0335157 A1 11/2014 Tange et al.
2021/0023008 A1* 1/2021 Nakai .................. C07D 405/14

FOREIGN PATENT DOCUMENTS

WO WO-2018170336 A1 * 9/2018 ........... A61K 9/5123
WO WO-2019188867 A1 * 10/2019 ........... C07D 405/14

(Continued)

OTHER PUBLICATIONS

Akita et al., "A Neutral Lipid Envelope—Type Nanoparticle Composed of a pH-Activated and Vitamin E-Scaffold Lipid-Like Material as a Platform for a Gene Carrier Targeting Renal Cell Carcinoma," *J. Control. Release*, 200: 97-105 (2015).

(Continued)

*Primary Examiner* — Dominic Lazaro

(74) *Attorney, Agent, or Firm* — Leydig, Voit & Mayer, Ltd.

(57) ABSTRACT

The present invention provides a lipid nanoparticle used for delivering a nucleic acid to a brain tissue, including an ionic lipid represented by the formula (1), phospholipid, cholesterol, and a dimyristoylglycerol PEG with a number average molecular weight of PEG chain of 4,000 to 6,000, wherein an amount of the dimyristoylglycerol PEG is 1 to 6 mol % with respect to the total of the ionic lipid represented by the formula (1), the phospholipid, and the cholesterol (the symbols in the formula (1) are as defined in the specification)

(Continued)

(1)

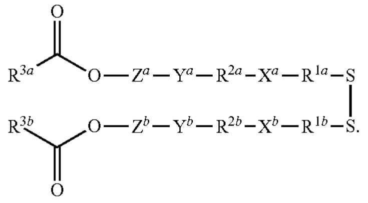

20 Claims, 6 Drawing Sheets

(72) Inventors: Yuta Nakai, Kawasaki (JP); Hidetaka Akita, Chiba (JP); Yu Sakurai, Chiba (JP); Hiroki Tanaka, Chiba (JP); Shoya Fujita, Chiba (JP)

(56) References Cited

FOREIGN PATENT DOCUMENTS

| | | | | |
|---|---|---|---|---|
| WO | WO-2019193347 A2 * | 10/2019 | .............. | A61P 25/28 |
| WO | 2020/142725 A1 | 7/2020 | | |
| WO | 2020/206231 A1 | 10/2020 | | |

OTHER PUBLICATIONS

Chen et al., "Influence of Particle Size on the in vivo Potency of Lipid Nanoparticle Formulations of siRNA," *J. Control. Release*, 235: 236-244 (2016).

Morille et al., "Progress in Developing Cationic Systems for Non-Viral Vector Systemic Gene Therapy against Cancer," *Biomaterials*, 29(24-25): 3477-3496 (2008).

Tanaka et al., "In Vivo Introduction of mRNA Encapsulated in Lipid Nanoparticles to Brain Neuronal Cells and Astrocytes via Intracerebroventricular Administration," *Mol. Pharm.*, 15(5): 2060-2067 (2018).

Japan Patent Office, International Search Report in International Patent Application No. PCT/JP2022/035636 (Dec. 13, 2022).

* cited by examiner

LIPID NANOPARTICLE USED FOR DELIVERING NUCLEIC ACID TO BRAIN TISSUE

TECHNICAL FIELD

The present invention relates to lipid nanoparticles used to deliver nucleic acids to brain tissues, and methods for delivering nucleic acids to brain tissues.

BACKGROUND ART

For practicalization of nucleic acid therapy, an effective and safe nucleic acid delivery carrier is demanded. While virus vectors are nucleic acid delivery carriers with good expression efficiency, they have practical problems from the aspect of safety. Therefore, the development of non-viral nucleic acid delivery carriers that can be used more safely is ongoing. Among them, lipid nanoparticles that are carriers using ionic lipids are non-viral nucleic acid delivery carriers most generally used at present.

Ionic lipids are largely constituted of amine moiety and lipid moiety. The amine moiety, which is protonated under acidic conditions, interacts electrostatically with nucleic acids, which are polyanions, to form lipid nanoparticles, which promotes uptake into cells and delivers nucleic acids into cells.

A known ionic lipid that is generally widely used is, for example, 1,2-dioleoyl-3-dimethylammonium propane (DODAP). It is known that by combining known ionic lipids with phospholipids, cholesterol, and PEG lipids, lipid nanoparticles can be formed and nucleic acids can be delivered into cells (Non Patent Literature 1).

Patent Literature 1 describes an ionic lipid having a structure in which compounds consisting of one or two amine moieties and one lipid moiety are connected by a biodegradable disulfide bond. This literature states that the ionic lipid can improve pharmacokinetics such as blood stability and tumor targeting, and that by changing the structure around the amine moiety, the pKa of a lipid membrane structure can be adjusted to a value advantageous for endosomal escape in cells, and further that it has the effect of dissociating nucleic acids from lipid membrane structures by utilizing the cleavage of disulfide bonds within cells. In fact, since it shows higher nucleic acid delivery efficiency compared to a known ionic lipid DODAP, it is clear that this ionic lipid can achieve improvement of the intracellular dynamics such as improvement of the delivery efficiency of nucleic acids into the cytoplasm and the like.

In Patent Literature 2, a lipid membrane structure is shown that has enhanced ability to fuse with endosomal membrane and has further improved efficiency of nucleic acid introduction into the cytoplasm, by using an ionic lipid having, in addition to a tertiary amine moiety and disulfide bond, an aromatic ring introduced near the lipid moiety.

As described above, ionic lipids with improved intracellular dynamics have been developed by increasing endosomal escape efficiency and membrane fusion ability. On the other hand, in order for lipid nanoparticles made of ionic lipids to exhibit more practical effects as nucleic acid delivery carriers in vivo, directivity to target organs and cells is demanded.

one of the PEG lipids widely used in lipid nanoparticles is dimyristoylglycerol PEG (DMG-PEG). It is known that when lipid nanoparticles using DMG-PEG with a PEG number average molecular weight of 2000 are administered into the blood, the PEG lipids gradually dissociate from the lipid nanoparticles in the blood, and apolipoprotein E (ApoE) present in the blood adheres to lipid nanoparticles, thus increasing its accumulation in the liver where ApoE receptors are expressed (Non Patent Literature 2).

As lipid nanoparticles that have been given directivity to organs other than the liver, for example, lipid nanoparticles obtained using, as a PEG lipid, distearoylglycerol PEG (DSG-PEG) having a stearic acid-derived hydrophobic group, instead of DMG-PEG having a myristic acid-derived hydrophobic group can be mentioned (Non Patent Literature 3). Compared to DMG-PEG, DSG-PEG does not easily dissociate from lipid nanoparticles in the blood. Therefore, DSG-PEG avoids adhesion of ApoE in the blood, suppresses accumulation in the liver, and shows high retention in the blood, as a result of which increases accumulation in tumors.

As described above, there are known multiple lipid nanoparticles with improved intracellular dynamics and multiple lipid nanoparticles with controlled organ accumulation after intravenous injection by changing PEG lipid, which is one of the constituent components. However, there is a wide variety of organs and cells that can be targets for drug discovery, and the development of lipid nanoparticles having directivity to various organs and cells is demanded.

Among organs, the brain is an organ into which delivery of drug is extremely difficult because the transfer of substances from the blood to the brain tissue is strictly restricted by the blood-brain barrier that exists in the intracerebral capillary. Because of this, cerebral neurosis includes many intractable diseases for which no effective treatment method exists. Thus, lipid nanoparticles to efficiently deliver therapeutic nucleic acids to the brain are desired.

Non Patent Literature 4 describes an example in which a nucleic acid was delivered to brain tissue by directly administering lipid nanoparticles encapsulating nucleic acid into the cerebral ventricle. However, direct administration of drugs into the cerebral ventricle places a heavy burden on patients, and a low-invasive method is desired.

As described above, while attempts have been made to deliver nucleic acids to the brain by using lipid nanoparticles, there is no example of the development of lipid nanoparticles that can efficiently deliver nucleic acids to the brain by a low-invasive method.

CITATION LIST

Patent Literature

[Patent Literature 1]
US 2014/0335157 A1
[Patent Literature 2]
WO 2019/188867 A1

Non Patent Literature

[Non Patent Literature 1]
Biomaterials, 29(24-25): 3477-3496 (2008)
[Non Patent Literature 2]
J. Control. Release, 235: 236-244 (2016)
[Non Patent Literature 3]
J. Control. Release, 200: 97-105 (2015)
[Non Patent Literature 4]
Mol. Pharmaceutics, 15(5): 2060-2067 (2018)

SUMMARY OF INVENTION

Technical Problem

An object of the present invention is to provide lipid nanoparticles that can efficiently deliver nucleic acids to brain tissues, and to provide a method for delivering nucleic acids to brain tissues by using the lipid nanoparticles.

Solution to Problem

The present inventors have conducted intensive studies in view of the above-mentioned problems and found that lipid nanoparticles produced using an ionic lipid that has a pKa suitable for endosomal escape and is specifically decomposed in a reducing environment within cells, and a specific ratio of dimyristoylglycerol PEG represented by the following formula (2) can efficiently deliver nucleic acids to brain tissues. The present invention based on this finding is as follows.

[1] A lipid nanoparticle used for delivering a nucleic acid to a brain tissue, comprising an ionic lipid represented by the formula (1):

(1)

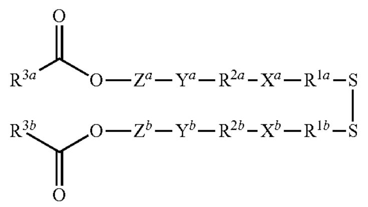

(in the formula (1), $R^{1a}$ and $R^{1b}$ are each independently an alkylene group having 1 to 6 carbon atoms, $X^a$ and $X^b$ are each independently an acyclic alkyl tertiary amino group having 1 to 6 carbon atoms and one tertiary amino group, or a cyclic alkylene tertiary amino group having 2 to 5 carbon atoms and 1 to 2 tertiary amino groups, $R^{2a}$ and $R^{2b}$ are each independently an alkylene group or an oxydialkylene group each having not more than 8 carbon atoms, $Y^a$ and $Y^b$ are each independently an ester bond, an amide bond, a carbamate bond, an ether bond or a urea bond, $Z^a$ and $Z^b$ are each independently a divalent group derived from an aromatic compound having 3 to 16 carbon atoms and at least one aromatic ring, and optionally having a hetero atom, and $R^{3a}$ and $R^{3b}$ are each independently a residue derived from a reaction product of a liposoluble vitamin having a hydroxyl group, and succinic anhydride or glutaric anhydride, or a residue derived from a reaction product of a sterol derivative having a hydroxyl group, and succinic anhydride or glutaric anhydride, or an aliphatic hydrocarbon group having 12 to 22 carbon atoms), phospholipid, cholesterol, and a dimyristoylglycerol PEG represented by the formula (2):

$$CH_2(OR^6)—CH(OR^7)—CH_2(OR^8) \quad (2)$$

(in the formula (2), two of $R^6$, $R^7$, and $R^8$ are myristoyl groups, and the remaining one is an alkyl group having 1 to 6 carbon atoms connected via a polyethylene glycol chain with a number average molecular weight of 4,000 to 6,000), wherein an amount of the dimyristoylglycerol PEG represented by the formula (2) is 1 to 6 mol % with respect to the total of the ionic lipid represented by the formula (1), the phospholipid, and the cholesterol.

[2] The lipid nanoparticle of the aforementioned [1], wherein lipids constituting the lipid nanoparticle consist of the ionic lipid represented by the formula (1), the phospholipid, the cholesterol, and the dimyristoylglycerol PEG represented by the formula (2).

[3] The lipid nanoparticle of the aforementioned [1] or [2], wherein the ionic lipid represented by the formula (1) is an ionic lipid represented by the following formula:

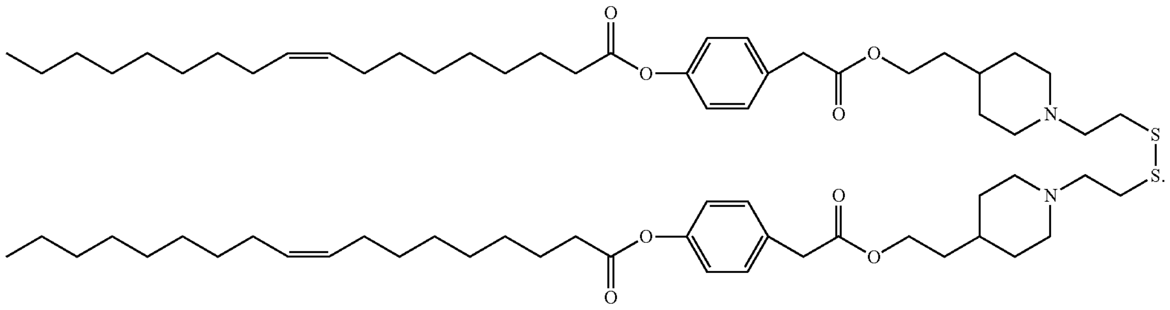 [SMILES: CCCCCCCC/C=C\CCCCCCCC(=O)Oc1ccc(CC(=O)OCCC2CCN(CCSSCCN3CCC(CCOC(=O)Cc4ccc(OC(=O)CCCCCCC/C=C\CCCCCCCC)cc4)CC3)CC2)cc1]

[4] The lipid nanoparticle of any one of the aforementioned [1] to [3], wherein the phospholipid is 1,2-dioleoyl-sn-glycero-3-phosphocholine.

[5] The lipid nanoparticle of any one of the aforementioned [1] to [4], wherein an amount of the ionic lipid represented by the formula (1) is 15 to 70 mol %, an amount of the phospholipid is 5 to 25 mol %, and an amount of the cholesterol is 25 to 80 mol %, with respect to the total of the ionic lipid represented by the formula (1), the phospholipid, and the cholesterol.

[6] A method for delivering a nucleic acid to a brain tissue, comprising transnasally administering the lipid nanoparticle of any one of the aforementioned [1] to [5] that encapsulates the nucleic acid to a subject.

Advantageous Effects of Invention

The lipid nanoparticles of the present invention can efficiently deliver a nucleic acid to a brain tissue.

BRIEF DESCRIPTION OF DRAWINGS

FIG. 5-1 is a diagram showing the effect of the number of administration (one administration to each of right and left nasal cavities as one set, same in the following diagrams) on the brain migration of mRNA-encapsulating LNP during in vivo administration FIG. 5-2 is a diagram showing the effect of the number of administration on the brain migration of mRNA-encapsulating LNP (left) and expression of the mRNA in the brain (right) during in vivo administration.

FIG. 6-1 is a diagram showing that the lipid composition and dosage optimized in the present invention are remarkably superior to the lipid composition and dosage for liver migration, with respect to the brain migration of mRNA-encapsulating LNP during in vivo administration.

FIG. 6-2 is a diagram showing that the lipid composition and dosage optimized in the present invention are significantly superior to the lipid composition and dosage for liver migration, with respect to the brain migration of mRNA-encapsulating LNP (left) and expression of the mRNA in the brain (right) during in vivo administration.

DESCRIPTION OF EMBODIMENTS

Figure 1:
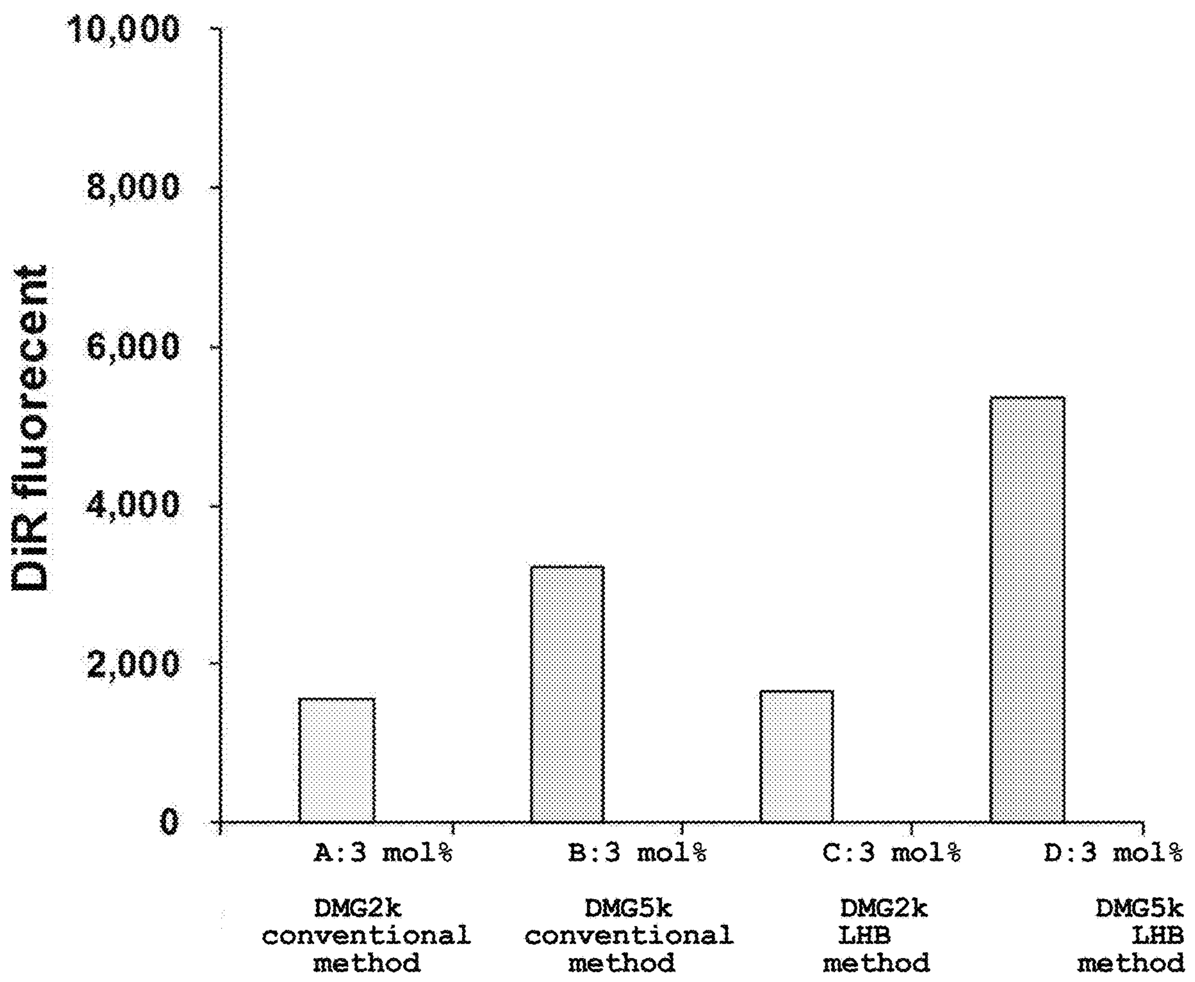
FIG. 1 is a diagram showing the effect of the molecular weight and administration method of the PEG chain of PEG lipid (DMG-PEG) on the brain migration of LNP.

While the embodiments of the present invention are explained in the following, the present invention is not limited thereto.

The present invention relates to lipid nanoparticles containing an ionic lipid represented by the formula (1) (i.e., ionic lipid having a tertiary amino group, a lipid moiety, and a disulfide bond as a biodegradable group), phospholipid, cholesterol, and dimyristoylglycerol PEG represented by the formula (2), and methods for delivering nucleic acids to brain tissues by using the lipid nanoparticles.

Lipid Nanoparticles

In the present specification, the "lipid nanoparticle" (Lipid Nano Particle, sometimes to be abbreviated as "LNP" in the present specification) means a particle having a membrane structure wherein the hydrophilic groups of amphiphilic lipid are arranged in the interface, facing the aqueous phase side, and having a particle size of less than 1 μm, and the "amphiphilic lipid" means a lipid having both a hydrophilic group and a hydrophobic group.

The particle size of the lipid nanoparticle of the present invention is preferably 10 nm to 500 nm, more preferably 30 nm to 300 nm. The particle size can be measured by using a particle size distribution measuring device such as Zetasizer Nano (Malvern) or the like. The particle size of the lipid nanoparticles can be appropriately adjusted by the method for producing the lipid nanoparticles. In the present specification, the "particle size" means an average particle size (number average) measured by a dynamic light scattering method.

Examples of the amphiphilic lipid include ionic lipid, phospholipid, PEG lipid, and the like. In the present specification, "PEG" means polyethylene glycol, "PEG lipid" means a lipid modified with PEG, and "Y modified with X" (e.g., X:PEG, Y:lipid) means Y bound by X. In other words, "PEG lipid" means a lipid bound by PEG.

The lipid nanoparticles of the present invention may contain lipids other than the ionic lipid represented by the formula (1), phospholipid, cholesterol, and dimyristoylglycerol PEG represented by the formula (2) (hereinafter sometimes to be referred to as "other lipid"). Examples of other lipid include sterols other than cholesterol, and PEG lipids other than the dimyristoylglycerol PEG represented by the formula (2).

The amount of other lipid in the lipid nanoparticle of the present invention is preferably 0 to 50 mol %, more preferably 0 to 30 mol %, further preferably 0 to 10 mol %, with respect to the total amount of lipids in the lipid nanoparticle. As used herein, when, for example, lipid nanoparticles contain an ionic lipid represented by the formula (1), phospholipid, cholesterol, dimyristoylglycerol PEG represented by the formula (2), and other lipid as constituent components, "the total amount of lipids in the lipid nanoparticle" means "the total amount of an ionic lipid represented by the formula (1), phospholipid, cholesterol, dimyristoylglycerol PEG represented by the formula (2), and other lipid". In the present specification, the "amount of B (mol %) with respect to A" means the "100× amount of B (mol)/amount of A (mol)". For example, the "amount of other lipid (mol %) with respect to the total amount of lipids" means the "100× amount of other lipid (mol)/total amount of lipid (mol)".

Most preferably, other lipids are not used in the present invention, i.e., lipids constituting the lipid nanoparticles of the present invention consist of an ionic lipid represented by the formula (1), phospholipid, cholesterol, and a dimyristoylglycerol PEG represented by the formula (2).

Ionic Lipid

The ionic lipid used in the present invention is an ionic lipid represented by the following formula (1) (sometimes to be abbreviated as "ionic lipid (1)" in the present specification). Only one kind of ionic lipid (1) may be used, or two or more kinds thereof may be used in combination.

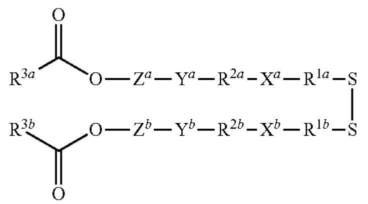
(1)

(in the formula (1), $R^{1a}$ and $R^{1b}$ are each independently an alkylene group having 1 to 6 carbon atoms, $X^a$ and $X^b$ are each independently an acyclic alkyl tertiary amino group having 1 to 6 carbon atoms and one tertiary amino group, or a cyclic alkylene tertiary amino group having 2 to 5 carbon atoms and 1 to 2 tertiary amino groups, $R^{2a}$ and $R^{2b}$ are each independently an alkylene group or an oxydialkylene group each having not more than 8 carbon atoms, $Y^a$ and $Y^b$ are each independently an ester bond, an amide bond, a carbamate bond, an ether bond or a urea bond, $Z^a$ and $Z^b$ are each independently a divalent group derived from an aromatic compound having 3 to 16 carbon atoms and at least one aromatic ring, and optionally having a hetero atom, and $R^{3a}$ and $R^{3b}$ are each independently a residue derived from a reaction product of a liposoluble vitamin having a hydroxyl group, and succinic anhydride or glutaric anhydride, or a residue derived from a reaction product of a sterol derivative having a hydroxyl group, and succinic anhydride or glutaric anhydride, or an aliphatic hydrocarbon group having 12 to 22 carbon atoms).

$R^{1a}$ and $R^{1b}$ are each independently an alkylene group having 1 to 6 carbon atoms, and may be linear or branched, preferably linear. The carbon number of the alkylene group is preferably 1 to 4, more preferably 1 to 2. Specific examples of the alkylene group having 1 to 6 carbon atoms include methylene group, ethylene group, trimethylene group, isopropylene group, tetramethylene group, isobutylene group, pentamethylene group, neopentylene group, and the like. Preferably, $R^1$ and $R^{1b}$ are each independently a methylene group, an ethylene group, a trimethylene group, an isopropylene group, or a tetramethylene group, most preferably an ethylene group.

$R^1$ may be the same as or different from $R^b$, and $R^1$ is preferably the same group as $R^b$.

$X^a$ and $X^b$ are each independently an acyclic alkyl tertiary amino group having 1 to 6 carbon atoms and one tertiary amino group, or a cyclic alkylene tertiary amino group having 2 to 5 carbon atoms and 1 to 2 tertiary amino groups, preferably each independently a cyclic alkylene tertiary amino group having 2 to 5 carbon atoms and 1 to 2 tertiary amino groups.

The alkyl group having 1 to 6 carbon atoms in the acyclic alkyl tertiary amino group having 1 to 6 carbon atoms and one tertiary amino group may be linear, branched or cyclic. The alkyl group preferably has a carbon number of 1 to 3. Specific examples of the alkyl group having 1 to 6 carbon atoms include methyl group, ethyl group, propyl group, isopropyl group, n-butyl group, sec-butyl group, isobutyl group, tert-butyl group, pentyl group, isopentyl group, neopentyl group, tert-pentyl group, 1,2-dimethylpropyl group, 2-methylbutyl group, 2-methylpentyl group, 3-methylpentyl group, 2,2-dimethylbutyl group, 2,3-dimethylbutyl group, cyclohexyl group, and the like, preferably methyl group, ethyl group, propyl group, or isopropyl group, most preferably methyl group.

A preferred specific structure of the acyclic alkyl tertiary amino group having 1 to 6 carbon atoms and one tertiary amino group is represented by $X^1$.

$X^1 =$ 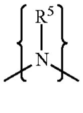

$R^5$ in $X^1$ is an alkyl group having 1 to 6 carbon atoms, which may be linear, branched or cyclic. The alkyl group preferably has a carbon number of 1 to 3. Specific examples of the alkyl group having 1 to 6 carbon atoms include methyl group, ethyl group, propyl group, isopropyl group, n-butyl group, sec-butyl group, isobutyl group, tert-butyl group, pentyl group, isopentyl group, neopentyl group, tert-pentyl, 1,2-dimethylpropyl group, 2-methylbutyl group, 2-methylpentyl group, 3-methylpentyl group, 2,2-dimethylbutyl group, 2,3-dimethylbutyl group, cyclohexyl group, and the like, preferably methyl group, ethyl group, propyl group, or isopropyl group, most preferably methyl group.

The carbon number of the cyclic alkylene tertiary amino group having 2 to 5 carbon atoms and 1 to 2 tertiary amino groups is preferably 4 to 5. The cyclic alkylene tertiary amino group having 2 to 5 carbon atoms and 1 to 2 tertiary amino groups is specifically an aziridylene group, an azetidylene group, a pyrrolidylene group, a piperidylene group, an imidazolidylene group, or a piperazylene group, preferably a pyrrolidylene group, a piperidylene group, or a piperazylene group, most preferably a piperidylene group.

A preferred specific structure of the cyclic alkylene tertiary amino group having 2 to 5 carbon atoms and one tertiary amino group is represented by $X^2$.

$X^2 =$ 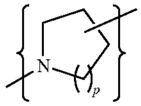

The p in $X^2$ is 1 or 2. When p is 1, $X^2$ is a pyrrolidylene group, and when p is 2, $X^2$ is a piperidylene group. Preferably, p is 2.

A preferred specific structure of the cyclic alkylene tertiary amino group having 2 to 5 carbon atoms and two tertiary amino groups is represented by $X^3$.

$X^3 =$ 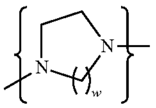

The w in $X^3$ is 1 or 2. When w is 1, $X^3$ is an imidazolidylene group, and when w is 2, $X^3$ is a piperazylene group.

$X^a$ may be the same as or different from $X^b$, and $X^a$ is preferably the same group as $X^b$.

$R^{2a}$ and $R^{2b}$ are each independently an alkylene group or an oxydialkylene group each having not more than 8 carbon atoms, preferably each independently an alkylene group having not more than 8 carbon atoms.

The alkylene group having not more than 8 carbon atoms may be linear or branched, preferably linear. The number of carbons contained in the alkylene group is preferably not more than 6, most preferably not more than 4. Specific examples of the alkylene group having not more than 8 carbon atoms include methylene group, ethylene group, trimethylene group, isopropylene group, tetramethylene group, isobutylene group, pentamethylene group, hexamethylene group, heptamethylene group, octamethylene group, and the like, preferably methylene group, ethylene group, trimethylene group, or tetramethylene group, most preferably ethylene group.

In the present specification, the "oxydialkylene group having not more than 8 carbon atoms" means alkylene groups via an ether bond (alkylene-O-alkylene, in other words, "alkyleneoxyalkylene group"), wherein the total carbon number of the two alkylene groups present is 8 or below. The two alkylene groups present may be the same or different, preferably the same. Specific examples of the oxydialkylene group having not more than 8 carbon atoms include oxydimethylene group, oxydiethylene group, oxydi(trimethylene) group (i.e., trimethyleneoxytrimethylene group), oxydi(tetramethylene) group (i.e., tetramethyleneoxytetramethylene group), and the like. Preferably, it is an oxydimethylene group, an oxydiethylene group, or an oxydi (tetramethylene) group, most preferably an oxydiethylene group.

$R^{2a}$ may be the same as or different from $R^{2b}$, and $R^{2a}$ is preferably the same group as $R^{2b}$.

$Y^a$ and $Y^b$ are each independently an ester bond, an amide bond, a carbamate bond, an ether bond or a urea bond, preferably each independently an ester bond, an amide bond or a carbamate bond, more preferably each independently an ester bond or an amide bond, most preferably each an ester bond. The direction of the bond of $Y^a$ and $Y^b$ is not limited. When $Y^a$ and $Y^b$ are ester bonds, the structure of $-Z^a-CO-O-R^{2a}-$ or $-Z^b-CO-O-R^{2b}-$ is preferably shown.

$Y^a$ may be the same as or different from $Y^b$, and $Y^a$ is preferably the same group as $Y^b$.

$Z^a$ and $Z^b$ are each independently a divalent group derived from an aromatic compound having 3 to 16 carbon atoms and at least one aromatic ring, and optionally having a hetero atom. The number of carbons contained in the aromatic compound is preferably 6 to 12, most preferably 6 to 7. The aromatic ring contained in the aromatic compound is preferably one.

As the kind of the aromatic ring contained in the aromatic compound having 3 to 16 carbon atoms, benzene ring, naphthalene ring, and anthracene ring can be mentioned for aromatic hydrocarbocycle, and imidazole ring, pyrazole ring, oxazole ring, isoxazole ring, thiazole ring, isothiazole ring, triazine ring, pyrrole ring, furan ring, thiophene ring, pyrimidine ring, pyridazine ring, pyrazine ring, pyridine ring, purine ring, pteridine ring, benzimidazole ring, indole ring, benzofuran ring, quinazoline ring, phthalazine ring, quinoline ring, isoquinoline ring, coumarin ring, chromone ring, benzodiazepine ring, phenoxazine ring, phenothiazine ring, acridine ring, and the like can be mentioned for aromatic heterocycle. It is preferably a benzene ring, a naphthalene ring, or an anthracene ring, most preferably a benzene ring.

The aromatic ring may have a substituent. Examples of the substituent include acyl group having 2 to 4 carbon atoms, alkoxycarbonyl group having 2 to 4 carbon atoms, alkylcarbamoyl group having 2 to 4 carbon atoms, acyloxy group having 2 to 4 carbon atoms, acylamino group having 2 to 4 carbon atoms, alkoxycarbonylamino group having 2 to 4 carbon atoms, fluorine atom, chlorine atom, bromine atom, iodine atom, alkylsulfanyl group having 1 to 4 carbon atoms, alkylsulfonyl group having 1 to 4 carbon atoms, arylsulfonyl group having 6 to 10 carbon atoms, nitro group, trifluoromethyl group, cyano group, alkyl group having 1 to 4 carbon atoms, ureido group, alkylureido group having 2 to 4 carbon atoms, alkoxy group having 1 to 4 carbon atoms, aryl group having 6 to 10 carbon atoms, aryloxy group having 6 to 10 carbon atoms, and the like. Preferred examples include acetyl group, methoxycarbonyl group, methylcarbamoyl group, acetoxy group, acetamido group, methoxycarbonylamino group, fluorine atom, chlorine atom, bromine atom, iodine atom, methylsulfanyl group, phenylsulfonyl group, nitro group, trifluoromethyl group, cyano group, methyl group, ethyl group, propyl group, isopropyl group, tert-butyl group, ureido group, methoxy group, ethoxy group, propoxy group, isopropoxy group, tert-butoxy group, phenyl group, phenoxy group, and the like.

A preferred specific structure of $Z^a$ and $Z^b$ is $Z^1$.

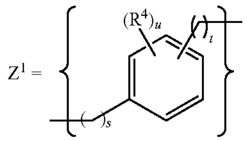

wherein s is an integer of 0 to 3, t is an integer of 0 to 3, u is an integer of 0 to 4, and $R^4$ in the number of u are each independently a substituent.

The s in $Z^1$ is preferably an integer of 0 to 1, more preferably 0.

The t in $Z^1$ is preferably an integer of 0 to 2, more preferably 1.

The u in $Z^1$ is preferably an integer of 0 to 2, more preferably an integer of 0 to 1.

The $R^4$ in $Z^1$ is a substituent of an aromatic ring (benzene ring) contained in the aromatic compound having 3 to 16 carbon atoms which does not inhibit the reaction in the synthesis process of an ionic lipid. Examples of the substituent include acyl group having 2 to 4 carbon atoms, alkoxycarbonyl group having 2 to 4 carbon atoms, alkylcarbamoyl group having 2 to 4 carbon atoms, acyloxy group having 2 to 4 carbon atoms, acylamino group having 2 to 4 carbon atoms, alkoxycarbonylamino group having 2 to 4 carbon atoms, fluorine atom, chlorine atom, bromine atom, iodine atom, alkylsulfanyl group having 1 to 4 carbon atoms, alkylsulfonyl group having 1 to 4 carbon atoms, arylsulfonyl group having 6 to 10 carbon atoms, nitro group, trifluoromethyl group, cyano group, alkyl group having 1 to 4 carbon atoms, ureido group, alkylureido group having 2 to 4 carbon atoms, alkoxy group having 1 to 4 carbon atoms, aryl group having 6 to 10 carbon atoms, aryloxy group having 6 to 10 carbon atoms, and the like. Preferred examples include acetyl group, methoxycarbonyl group, methylcarbamoyl group, acetoxy group, acetamido group, methoxycarbonylamino group, fluorine atom, chlorine atom, bromine atom, iodine atom, methylsulfanyl group, phenylsulfonyl group, nitro group, trifluoromethyl group, cyano group, methyl group, ethyl group, propyl group, isopropyl group, tert-butyl group, ureido group, methoxy group, ethoxy group, propoxy group, isopropoxy group, tert-butoxy group, phenyl group, phenoxy group, and the like. When $R^4$ is present in plurality, each $R^4$ may be the same or different.

$Z^a$ may be the same as or different from $Z^b$, and $Z^a$ is preferably the same group as $Z^b$.

$R^{3a}$ and $R^{3b}$ are each independently a residue derived from a reaction product of a liposoluble vitamin having a hydroxyl group, and succinic anhydride or glutaric anhydride, or a residue derived from a reaction product of a sterol derivative having a hydroxyl group, and succinic anhydride or glutaric anhydride, or an aliphatic hydrocarbon group having 12 to 22 carbon atoms, preferably each independently a residue derived from a reaction product of a liposoluble vitamin having a hydroxyl group, and succinic anhydride or glutaric anhydride, or an aliphatic hydrocarbon group having 12 to 22 carbon atoms, most preferably each independently an aliphatic hydrocarbon group having 12 to 22 carbon atoms.

Examples of the liposoluble vitamin having a hydroxyl group include retinol, ergosterol, 7-dehydrocholesterol, calciferol, cholecalciferol, dihydroergocalciferol, dihydrotachysterol, tocopherol, tocotrienol, and the like. The liposoluble vitamin having a hydroxyl group is preferably tocopherol.

Examples of the sterol derivative having a hydroxyl group include cholesterol, cholestanol, stigmasterol, R-sitosterol, lanosterol, ergosterol, and the like, preferably cholesterol or cholestanol.

The aliphatic hydrocarbon group having 12 to 22 carbon atoms may be linear or branched. The aliphatic hydrocarbon group may be saturated or unsaturated. In the case of an unsaturated aliphatic hydrocarbon group, the aliphatic hydrocarbon group generally contains 1 to 6, preferably 1 to 3, more preferably 1 to 2 unsaturated bonds. While the unsaturated bond includes a carbon-carbon double bond and a carbon-carbon triple bond, it is preferably a carbon-carbon double bond. The aliphatic hydrocarbon group has a carbon number of preferably 13 to 19, most preferably 13 to 17. While the aliphatic hydrocarbon group includes an alkyl group, an alkenyl group, an alkynyl group, and the like, it is preferably an alkyl group or an alkenyl group. Specific examples of the aliphatic hydrocarbon group having 12 to 22 carbon atoms include dodecyl group, tridecyl group, tetradecyl group, pentadecyl group, hexadecyl group, heptadecyl group, octadecyl group, nonadecyl group, icosyl group, henicosyl group, docosyl group, dodecenyl group, tridecenyl group, tetradecenyl group, pentadecenyl group, hexadecenyl group, heptadecenyl group, octadecenyl group, nonadecenyl group, icosenyl group, henicosenyl group, docosenyl group, decadienyl group, tridecadienyl group, tetradecadienyl group, pentadecadienyl group, hexadecadienyl group, heptadecadienyl group, octadecadienyl group, nonadecadienyl group, icosadienyl group, henicosadienyl group, docosadienyl group, octadecatrienyl group, icosatrienyl group, icosatetraenyl group, icosapentaenyl group, docosahexaenyl group, isostearyl group, 1-hexylheptyl group, 1-hexylnonyl group, 1-octylnonyl group, 1-octylundecyl group, 1-decylundecyl group, and the like. The aliphatic hydrocarbon group having 12 to 22 carbon atoms is preferably a tridecyl group, a pentadecyl group, a heptadecyl group, a nonadecyl group, a heptadecenyl group, a heptadecadienyl group, or a 1-hexylnonyl group, particularly preferably a tridecyl group, a heptadecyl group, a heptadecenyl group, or a heptadecadienyl group.

In one embodiment of the present invention, the aliphatic hydrocarbon group having 12 to 22 carbon atoms for $R^{3a}$ or $R^{3b}$ is derived from fatty acid. In this case, the carbonyl carbon derived from fatty acid is contained in —CO—O— in the formula (1). A specific example of the aliphatic hydrocarbon group is a heptadecadienyl group when linoleic acid is used as the fatty acid, or a heptadecenyl group when oleic acid is used as the fatty acid.

$R^{3a}$ may be the same as or different from $R^{3b}$, and $R^{3a}$ is preferably the same group as $R^{3b}$.

In one embodiment of the present invention, $R^{1a}$ is the same as $R^{1b}$, $X^a$ is the same as $X^b$, $R^{2a}$ is the same as $R^{2b}$, $Y^a$ is the same as $Y^b$, $Z^a$ is the same as $Z^b$, and $R^{3a}$ is the same as $R^{3b}$.

Preferred examples of ionic lipid (1) include the following ionic lipids.

[Ionic Lipid (1-1)]

Ionic lipid (1) wherein $R^1$ and $R^b$ are each independently an alkylene group having 1 to 6 carbon atoms (e.g., methylene group, ethylene group);

$X^a$ and $X^b$ are each independently an acyclic alkyl tertiary amino group having 1 to 6 carbon atoms and one tertiary amino group (e.g., —$N(CH_3)$—), or a cyclic alkylene tertiary amino group having 2 to 5 carbon atoms and 1 to 2 tertiary amino groups (e.g., piperidylene group);

$R^{2a}$ and $R^{2b}$ are each independently an alkylene group having not more than 8 carbon atoms (e.g., methylene group, ethylene group, trimethylene group);

$Y^a$ and $Y^b$ are each independently an ester bond or an amide bond;

$Z^a$ and $Z^b$ are each independently a divalent group derived from an aromatic compound having 3 to 16 carbon atoms and at least one aromatic ring, and optionally having a hetero atom (e.g., —$C_6H_4$—$CH_2$—, —$CH_2$—$C_6H_4$—$CH_2$—); and $R^{3a}$ and $R^{3b}$ are each independently a residue derived from a reaction product of a liposoluble vitamin having a hydroxyl group (e.g., tocopherol), and succinic anhydride or glutaric anhydride, or an aliphatic hydrocarbon group having 12 to 22 carbon atoms (e.g., heptadecenyl group, heptadecadienyl group, 1-hexylnonyl group).

[Ionic Lipid (1-2)]

Ionic lipid (1) wherein $R^{1a}$ and $R^{1b}$ are each independently an alkylene group having 1 to 4 carbon atoms (e.g., methylene group, ethylene group);

$X^a$ and $X^b$ are each independently an acyclic alkyl tertiary amino group having 1 to 3 carbon atoms and one tertiary amino group (e.g., —$N(CH_3)$—), or a cyclic alkylene tertiary amino group having 2 to 5 carbon atoms and one tertiary amino group (e.g., piperidylene group);

$R^{2a}$ and $R^{2b}$ are each independently an alkylene group having not more than 6 carbon atoms (e.g., methylene group, ethylene group, trimethylene group);

$Y^a$ and $Y^b$ are each independently an ester bond or an amide bond;

$Z^a$ and $Z^b$ are each independently a divalent group derived from an aromatic compound having 6 to 12 carbon atoms and one aromatic ring, and optionally having a hetero atom (e.g., —$C_6H_4$—$CH_2$—, —$CH_2$—$C_6H_4$—$CH_2$—); and $R^{3a}$ and $R^{3b}$ are each independently a residue derived from a reaction product of a liposoluble vitamin having a hydroxyl group (e.g., tocopherol), and succinic anhydride, or an aliphatic hydrocarbon group having 13 to 19 carbon atoms (e.g., heptadecenyl group, heptadecadienyl group, 1-hexylnonyl group).

[Ionic Lipid (1-3)]

Ionic lipid (1) wherein $R^{1a}$ and $R^{1b}$ are each independently an alkylene group having 1 to 2 carbon atoms (e.g., methylene group, ethylene group);

$X^a$ and $X^b$ are each independently $X^1$:

$X^1$ =

wherein $R^5$ is an alkyl group having 1 to 3 carbon atoms (e.g., a methyl group), or $X^2$:

$X^2$ =
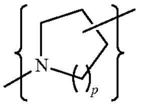

wherein p is 1 or 2;

$R^{2a}$ and $R^{2b}$ are each independently alkylene group having not more than 4 carbon atoms (e.g., methylene group, ethylene group, trimethylene group);

$Y^a$ and $Y^b$ are each independently an ester bond or an amide bond;

$Z^a$ and $Z^b$ are each independently $Z^1$:

$Z^1$ =

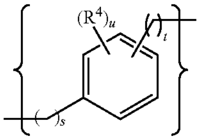

wherein s is an integer of 0 to 1, t is an integer of 0 to 2, u is an integer of 0 to 2 (preferably 0), and $R^4$ in the number of u are each independently a substituent; and $R^{3a}$ and $R^{3b}$ are each independently a residue derived from a reaction product of a liposoluble vitamin having a hydroxyl group (e.g., tocopherol) and succinic anhydride, or an aliphatic hydrocarbon group having 13 to 17 carbon atoms (e.g., heptadecenyl group, heptadecadienyl group, 1-hexylnonyl group).

Specific examples of ionic lipid (1) include the following O-Ph-P3C1, O-Ph-P4C1, O-Ph-P4C2, O-Bn-P4C2, E-Ph-P4C2, L-Ph-P4C2, HD-Ph-P4C2, O-Ph-amide-P4C2, and O-Ph-C3M.

TABLE 1-1

| name of ionic lipid | structure |
|---|---|
| O-Ph-P3C1 | 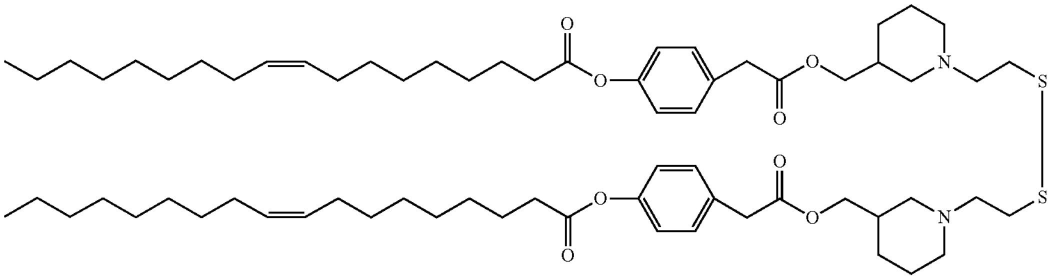 [SMILES: CCCCCCCC/C=C\CCCCCCCC(=O)Oc1ccc(CC(=O)OCC2CCCN(CCSSCCN3CCCC(COC(=O)Cc4ccc(OC(=O)CCCCCCC/C=C\CCCCCCCC)cc4)C3)C2)cc1] |
| O-Ph-P4C1 | 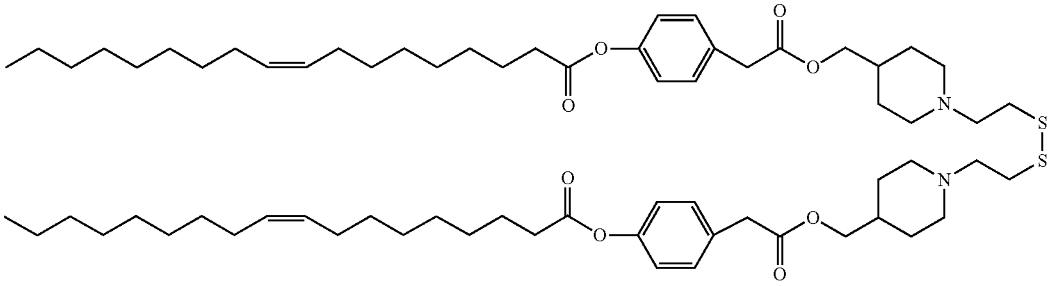 [SMILES: CCCCCCCC/C=C\CCCCCCCC(=O)Oc1ccc(CC(=O)OCC2CCN(CCSSCCN3CCC(COC(=O)Cc4ccc(OC(=O)CCCCCCC/C=C\CCCCCCCC)cc4)CC3)CC2)cc1] |
| O-Ph-P4C2 (or SS-OP) | 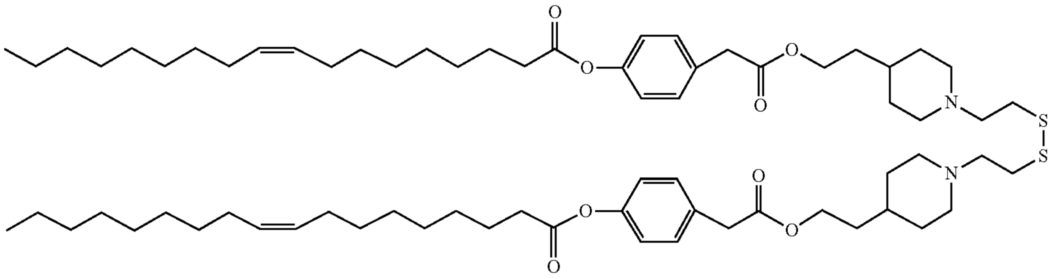 [SMILES: CCCCCCCC/C=C\CCCCCCCC(=O)Oc1ccc(CC(=O)OCCC2CCN(CCSSCCN3CCC(CCOC(=O)Cc4ccc(OC(=O)CCCCCCC/C=C\CCCCCCCC)cc4)CC3)CC2)cc1] |
| O-Bn-P4C2 | 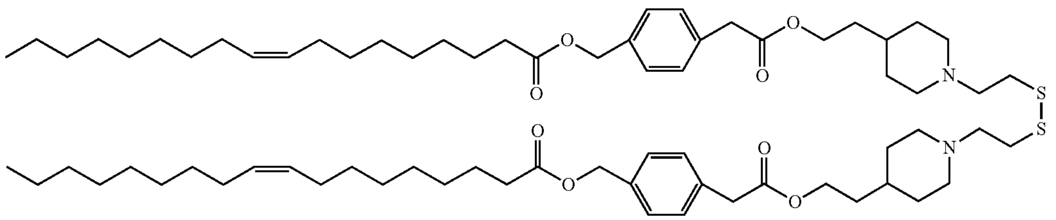 [SMILES: CCCCCCCC/C=C\CCCCCCCC(=O)OCc1ccc(CC(=O)OCCC2CCN(CCSSCCN3CCC(CCOC(=O)Cc4ccc(COC(=O)CCCCCCC/C=C\CCCCCCCC)cc4)CC3)CC2)cc1] |

TABLE 1-1-continued
| name of ionic lipid | structure |
| --- | --- |
| E-Ph-P4C2 (or SS-EP) | 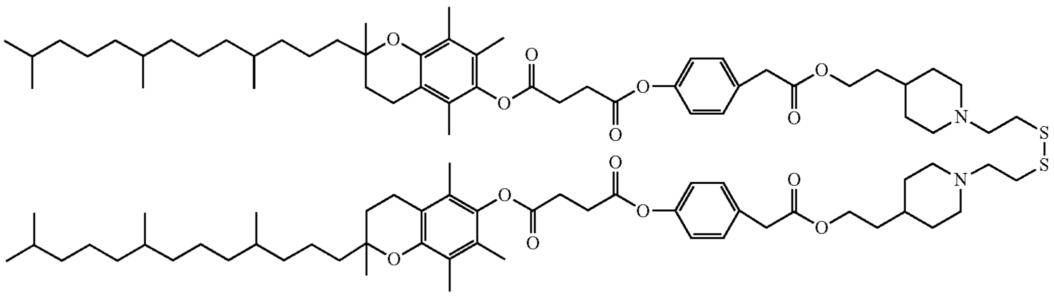 [SMILES: Cc1c(C)c2c(c(C)c1OC(=O)CCC(=O)Oc1ccc(CC(=O)OCCC3CCN(CCSSCCN4CCC(CCOC(=O)Cc5ccc(OC(=O)CCC(=O)Oc6c(C)c(C)c7c(c6C)CCC(C)(CCCC(C)CCCC(C)CCCC(C)C)O7)cc5)CC4)CC3)cc1)CCC(C)(CCCC(C)CCCC(C)CCCC(C)C)O2] |
TABLE 1-2
| name of ionic lipid | structure |
| --- | --- |
| L-Ph-P4C2 | 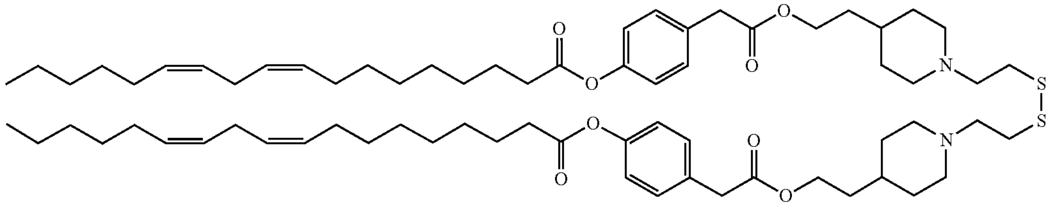 [SMILES: CCCCC/C=C\C/C=C\CCCCCCCC(=O)Oc1ccc(CC(=O)OCCC2CCN(CCSSCCN3CCC(CCOC(=O)Cc4ccc(OC(=O)CCCCCCC/C=C\C/C=C\CCCCC)cc4)CC3)CC2)cc1] |
| HD-Ph-P4C2 | 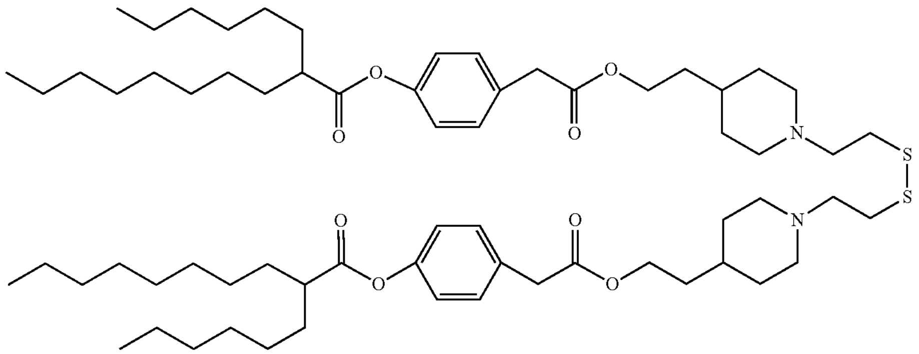 [SMILES: CCCCCCCCC(CCCCCC)C(=O)Oc1ccc(CC(=O)OCCC2CCN(CCSSCCN3CCC(CCOC(=O)Cc4ccc(OC(=O)C(CCCCCC)CCCCCCCC)cc4)CC3)CC2)cc1] |
| O-Ph-amide-P4C2 | 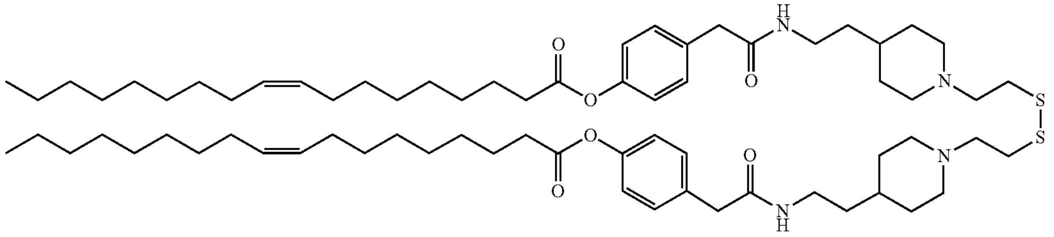 |

TABLE 1-2-continued

| name of ionic lipid | structure |
| --- | --- |
| O-Ph-C3M | 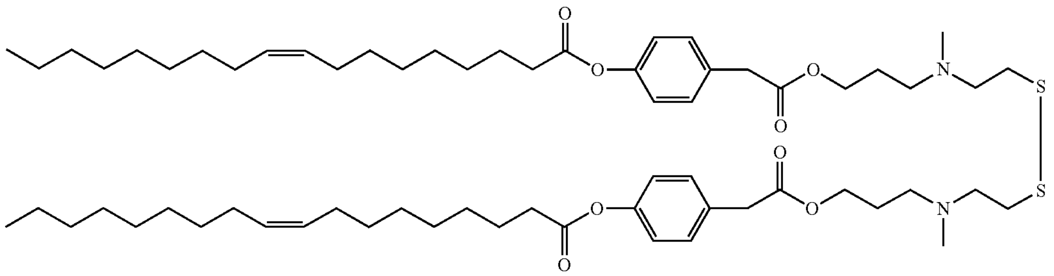 [SMILES: CCCCCCCC/C=C\CCCCCCCC(=O)Oc1ccc(CC(=O)OCCCN(C)CCSSCCN(C)CCCOC(=O)Cc2ccc(OC(=O)CCCCCCC/C=C\CCCCCCCC)cc2)cc1] |

Among the specific examples of ionic lipid (1), SS—OP is preferred. That is, ionic lipid (1) is preferably an ionic lipid represented by the following formula.

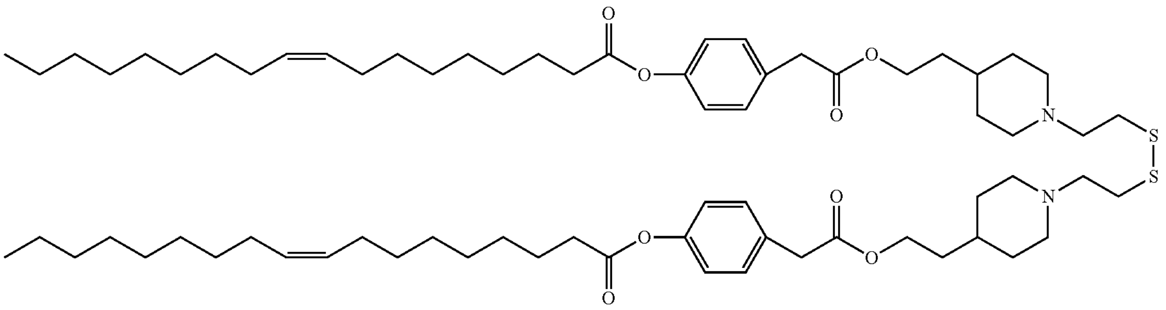 [SMILES: CCCCCCCC/C=C\CCCCCCCC(=O)Oc1ccc(CC(=O)OCCC2CCN(CCSSCCN3CCC(CCOC(=O)Cc4ccc(OC(=O)CCCCCCC/C=C\CCCCCCCC)cc4)CC3)CC2)cc1]

The amount of ionic lipid (1) in the lipid nanoparticle of the present invention is preferably 15 to 70 mol %, more preferably 15 to 55 mol %, further preferably 15 to 35 mol %, with respect to the total of ionic lipid (1), phospholipid, and cholesterol, from the aspects of efficiency of nucleic acid encapsulation, efficiency of intracellular release of nucleic acid, and stability of the lipid nanoparticles.

The ionic lipid (1) can be produced by a known method (e.g., the method described in WO 2019/188867 A1).

Phospholipid

The lipid nanoparticles of the present invention contain phospholipid. Only one kind of the phospholipid may be used, or two or more kinds thereof may be used in combination.

Examples of the phospholipid include 1,2-diacyl-sn-glycero-3-phosphocholine (PC), 1,2-diacyl-sn-glycero-3-phosphoethanolamine (PE), 1,2-diacyl-sn-glycero-3-phosphoserine (PS), 1,2-diacyl-sn-glycero-3-phosphoglycerol (PG), 1,2-diacyl-sn-glycero-3-phosphatidic acid (PA), lyso forms of these, and the like.

Specific examples of 1,2-diacyl-sn-glycero-3-phosphocholine (PC) include 1,2-didecanoyl-sn-glycero-3-phosphocholine (DDPC),
1,2-dilauroyl-sn-glycero-3-phosphocholine (DLPC),
1,2-dimyristoyl-sn-glycero-3-phosphocholine (DMPC),
1,2-dipalmitoyl-sn-glycero-3-phosphocholine (DPPC),
1,2-distearoyl-sn-glycero-3-phosphocholine (DSPC),
1,2-dioleoyl-sn-glycero-3-phosphocholine (DOPC),
1,2-dilinoleoyl-sn-glycero-3-phosphocholine (DLoPC),
1,2-dierucoyl-sn-glycero-3-phosphocholine (DEPC),
1-myristoyl-2-palmitoyl-sn-glycero-3-phosphocholine (MPPC),
1-myristoyl-2-stearoyl-sn-glycero-3-phosphocholine (MSPC),
1-palmitoyl-2-myristoyl-sn-glycero-3-phosphocholine (PMPC),
1-palmitoyl-2-stearoyl-sn-glycero-3-phosphocholine (PSPC),
1-palmitoyl-2-oleoyl-sn-glycero-3-phosphocholine (POPC), and
1-stearoyl-2-oleoyl-sn-glycero-3-phosphocholine (SOPC).

In the present specification, phospholipid may be sometimes indicated with the abbreviation thereof. For example, 1,2-diacyl-sn-glycero-3-phosphocholine is sometimes indicated as PC, and 1,2-didecanoyl-sn-glycero-3-phosphocholine is sometimes indicated as DDPC.

Specific examples of 1,2-diacyl-sn-glycero-3-phosphoethanolamine (PE) include 1,2-didecanoyl-sn-glycero-3-phosphoethanolamine (DDPE),
1,2-dilauroyl-sn-glycero-3-phosphoethanolamine (DLPE),
1,2-dimyristoyl-sn-glycero-3-phosphoethanolamine (DMPE),
1,2-dipalmitoyl-sn-glycero-3-phosphoethanolamine (DPPE),
1,2-distearoyl-sn-glycero-3-phosphoethanolamine (DSPE),
1,2-dioleoyl-sn-glycero-3-phosphoethanolamine (DOPE),
1,2-dilinoleoyl-sn-glycero-3-phosphoethanolamine (DLoPE),
1,2-dierucoyl-sn-glycero-3-phosphoethanolamine (DEPE), 1-myristoyl-2-palmitoyl-sn-glycero-3-phosphoethanolamine (MPPE),
1-myristoyl-2-stearoyl-sn-glycero-3-phosphoethanolamine (MSPE),
1-palmitoyl-2-myristoyl-sn-glycero-3-phosphoethanolamine (PMPE),
1-palmitoyl-2-stearoyl-sn-glycero-3-phosphoethanolamine (PSPE),
1-palmitoyl-2-oleoyl-sn-glycero-3-phosphoethanolamine (POPE), and
1-stearoyl-2-oleoyl-sn-glycero-3-phosphoethanolamine (SOPE).

Specific examples of 1,2-diacyl-sn-glycero-3-phosphoserine (PS) include
1,2-didecanoyl-sn-glycero-3-phosphoserine (DDPS),
1,2-dilauroyl-sn-glycero-3-phosphoserine (DLPS),
1,2-dimyristoyl-sn-glycero-3-phosphoserine (DMPS),
1,2-dipalmitoyl-sn-glycero-3-phosphoserine (DPPS),
1,2-distearoyl-sn-glycero-3-phosphoserine (DSPS),
1,2-dioleoyl-sn-glycero-3-phosphoserine (DOPS),
1,2-dilinoleoyl-sn-glycero-3-phosphoserine (DLoPS),
1,2-dierucoyl-sn-glycero-3-phosphoserine (DEPS),
1-myristoyl-2-palmitoyl-sn-glycero-3-phosphoserine (MPPS),
1-myristoyl-2-stearoyl-sn-glycero-3-phosphoserine (MSPS),
1-palmitoyl-2-myristoyl-sn-glycero-3-phosphoserine (PMPS),
1-palmitoyl-2-stearoyl-sn-glycero-3-phosphoserine (PSPS),
1-palmitoyl-2-oleoyl-sn-glycero-3-phosphoserine (POPS), and
1-stearoyl-2-oleoyl-sn-glycero-3-phosphoserine (SOPS).

Specific examples of 1,2-diacyl-sn-glycero-3-phosphoglycerol (PG) include
1,2-didecanoyl-sn-glycero-3-phosphoglycerol (DDPG),
1,2-dilauroyl-sn-glycero-3-phosphoglyceroi (DLPG),
1,2-dimyristoyl-sn-glycero-3-phosphoglycerol (DMPG),
1,2-dipalmitoyl-sn-glycero-3-phosphoglycerol (DPPG),
1,2-distearoyl-sn-glycero-3-phosphoglycerol (DSPG),
1,2-dioleoyl-sn-glycero-3-phosphoglycerol (DOPG),
1,2-dilinoleoyl-sn-glycero-3-phosphoglycerol (DLoPG),
1,2-dierucoyl-sn-glycero-3-phosphoglycerol (DEPG),
1-myristoyl-2-palmitoyl-sn-glycero-3-phosphoglycerol (MPPG),
1-myristoyl-2-stearoyl-sn-glycero-3-phosphoglycerol (MSPG),
1-palmitoyl-2-myristoyl-sn-glycero-3-phosphoglycerol (PMPG),
1-palmitoyl-2-stearoyl-sn-glycero-3-phosphoglycerol (PSPG),
1-palmitoyl-2-oleoyl-sn-glycero-3-phosphoglycerol (POPG), and
1-stearoyl-2-oleoyl-sn-glycero-3-phosphoglycerol (SOPG).

Specific examples of 1,2-diacyl-sn-glycero-3-phosphatidic acid (PA) include
1,2-didecanoyl-sn-glycero-3-phosphatidic acid (DDPA),
1,2-dilauroyl-sn-glycero-3-phosphatidic acid (DLPA),
1,2-dimyristoyl-sn-glycero-3-phosphatidic acid (DMPA),
1,2-dipalmitoyl-sn-glycero-3-phosphatidic acid (DPPA),
1,2-distearoyl-sn-glycero-3-phosphatidic acid (DSPA),
1,2-dioleoyl-sn-glycero-3-phosphatidic acid (DOPA),
1,2-dilinoleoyl-sn-glycero-3-phosphatidic acid (DLoPA),
1,2-dierucoyl-sn-glycero-3-phosphatidic acid (DEPA),
1-myristoyl-2-palmitoyl-sn-glycero-3-phosphatidic acid (MPPA),
1-myristoyl-2-stearoyl-sn-glycero-3-phosphatidic acid (MSPA),
1-palmitoyl-2-myristoyl-sn-glycero-3-phosphatidic acid (PMPA),
1-palmitoyl-2-stearoyl-sn-glycero-3-phosphatidic acid (PSPA),
1-palmitoyl-2-oleoyl-sn-glycero-3-phosphatidic acid (POPA), and
1-stearoyl-2-oleoyl-sn-glycero-3-phosphatidic acid (SOPA).

Phospholipid is preferably PC and/or PE. In one embodiment of the present invention, the phospholipid is more preferably at least one selected from the group consisting of DOPC, POPC, DOPE, and POPE. In another embodiment of the present invention, the phospholipid is more preferably at least one selected from the group consisting of DOPC, SOPC, POPC, DPPC, and DEPC. The phospholipid is further preferably DOPC.

The amount of the phospholipid in the lipid nanoparticle of the present invention is preferably 5 to 25 mol %, more preferably 5 to 20 mol %, further preferably 10 to 20 mol %, with respect to the total of ionic lipid (1), phospholipid, and cholesterol, from the aspects of efficiency of nucleic acid encapsulation, efficiency of intracellular release of nucleic acid, and stability of the lipid nanoparticles.

Cholesterol

The lipid nanoparticles of the present invention contain cholesterol. The amount of the cholesterol in the lipid nanoparticle of the present invention is preferably 25 to 80 mol %, more preferably 50 to 70 mol %, further preferably 55 to 65 mol %, with respect to the total of ionic lipid (1), phospholipid, and cholesterol, from the aspects of efficiency of nucleic acid encapsulation, efficiency of intracellular release of nucleic acid, and stability of the lipid nanoparticles.

Dimyristoylglycerol PEG

The lipid nanoparticles of the present invention contains a dimyristoylglycerol PEG represented by the formula (2):

$$CH_2(OR^6)—CH(OR^7)—CH_2(OR^8) \quad (2)$$

(in the formula (2), two of $R^6$, $R^7$, and Re are myristoyl groups, and the remaining one is an alkyl group having 1 to 6 carbon atoms connected via a polyethylene glycol (PEG) chain with a number average molecular weight of 4,000 to 6,000) (sometimes to be abbreviated as "dimyristoylglycerol PEG (2)" in the present specification).

The number average molecular weight of the PEG chain in the formula (2) is 4,000 to 6,000, preferably 4,500 to 5,500. The number average molecular weight of PEG used to form the PEG chain can be measured by gel permeation chromatography (GPC).

The alkyl group having 1 to 6 carbon atoms may be linear, branched or cyclic. The alkyl group preferably has a carbon number of 1 to 3. Specific examples of the alkyl group having 1 to 6 carbon atoms include methyl group, ethyl group, propyl group, isopropyl group, n-butyl group, sec-butyl group, isobutyl group, tert-butyl group, pentyl group, isopentyl group, neopentyl group, tert-pentyl group, 1,2-dimethylpropyl group, 2-methylbutyl group, 2-methylpentyl group, 3-methylpentyl group, 2,2-dimethylbutyl group, 2,3-dimethylbutyl group, cyclohexyl group, and the like. Preferred is a methyl group.

The amount of the dimyristoylglycerol PEG (2) in the lipid nanoparticle of the present invention is preferably 1 to 6 mol %, more preferably 2 to 5 mol %, further preferably 2 to 3 mol %, with respect to the total of ionic lipid (1), phospholipid, and cholesterol, from the aspects of efficiency of nucleic acid encapsulation, efficiency of intracellular release of nucleic acid, and stability of the lipid nanoparticles.

Optimal Composition

The optimal molar ratio of ionic lipid (1):phospholipid: cholesterol:dimyristoylglycerol PEG (2) in the lipid nanoparticle of the present invention is 25:15:60:3.

Production Method of Lipid Nanoparticles

The lipid nanoparticles of the present invention can be produced by dispersing a lipid material containing ionic lipid (1), phospholipid, cholesterol, and dimyristoylglycerol PEG (2) in a suitable dispersion medium (for example, aqueous dispersion medium, alcoholic dispersion medium), and performing an operation to induce organization as necessary.

Examples of the "operation to induce organization" for producing the lipid nanoparticles of the present invention include methods known per se such as ethanol dilution method using a microchannel or vortex, simple hydration method, sonication, heating, vortex, ether injecting method, French press method, cholic acid method, $Ca^{2+}$ fusion method, freeze-thaw method, reversed-phase evaporation method, and the like, preferably ethanol dilution method using a microchannel or vortex, further preferably ethanol dilution method using a microchannel. In the ethanol dilution method using a microchannel, for example, a dispersion containing lipid nanoparticles can be produced by mixing an acidic buffer containing a nucleic acid and an ethanol solution of a lipid by using NanoAssemblr (registered trademark) (Precision NanoSystems). The dispersion produced by this method contains lipid nanoparticles and a dispersion medium (acidic buffer and ethanol). The dispersion medium (particularly ethanol) can be removed, the dispersion medium (particularly buffer) can be exchanged, and the like by operations such as ultrafiltration, dialysis, dilution, and the like.

Method for Delivering Nucleic Acid to Brain Tissue

The present invention also provides a method for delivering a nucleic acid to a brain tissue, including administering the lipid nanoparticles encapsulating the nucleic acid of the present invention to a subject. The aforementioned lipid nanoparticles are preferably administered transnasally to a subject.

Examples of the nucleic acid include, but are not limited to, DNA, RNA, chimera nucleic acid of RNA, DNA/RNA hybrid and the like. While any single-stranded to triple-stranded nucleic acid can be used, it is preferably single-stranded or double-stranded. The nucleic acid may be a nucleotide having N-glycoside of purine or pyrimidine base, an oligomer having a non-nucleotide backbone (e.g., commercially available peptide nucleic acid (PNA) etc.), or an oligomer containing a special bond (said oligomer containing a nucleotide having a configuration permitting base pairing or attachment of base, which are found in DNA and RNA) and the like.

Furthermore, the nucleic acid may be, for example, a nucleic acid added with known modification, a nucleic acid with a label known in the field, a nucleic acid with a cap, a methylated nucleic acid, a nucleic acid with one or more natural nucleotides substituted by an analog, a nucleic acid with modified nucleotide, a nucleic acid having a non-charge bond (e.g., methylphosphonate, phosphotriester, phosphoramidate, carbamate and the like), a nucleic acid having a charged bond or sulfur-containing bond (e.g., phosphorothioate, phosphorodithioate, and the like), a nucleic acid having a side chain group such as protein (e.g., nuclease, nuclease inhibitor, toxin, antibody, signal peptide, poly-L-lysine, and the like), sugar (e.g., monosaccharide and the like), and the like, a nucleic acid containing an intercalating compound (e.g., acridine, psoralen, and the like), a nucleic acid containing a chelate compound (e.g., metal, radioactive metal, boron, oxidative metal, and the like), a nucleic acid containing an alkylating agent, or a nucleic acid containing a modified bond (e.g., a anomer-type nucleic acid and the like).

The type of the DNA that can be used in the present invention is not particularly limited, and can be selected as appropriate according to the purpose of use. Examples of the DNA include plasmid DNA, cDNA, antisense DNA, chromosomal DNA, PAC, BAC, CpG oligosaccharide, and the like. Preferred are plasmid DNA, cDNA and antisense DNA, and more preferred is plasmid DNA. A circular DNA such as plasmid DNA and the like can be digested as appropriate with a restriction enzyme and the like, and also used as a linear DNA.

The type of the RNA that can be used in the present invention is not particularly limited, and can be selected as appropriate according to the purpose of use. Examples of the RNA include siRNA, miRNA, shRNA, antisense RNA, messenger RNA (mRNA), single-stranded RNA genome, double-stranded RNA genome, RNA replicon, transfer RNA, ribosomal RNA, and the like, with preference given to siRNA, miRNA, shRNA, mRNA, antisense RNA, and RNA replicon.

The nucleic acid used in the present invention is preferably purified by a method generally used by those of ordinary skill in the art.

The nucleic acid to be used in the present invention is preferably one having a preventive and/or therapeutic activity against a given disease (prophylactic/therapeutic nucleic acid). Examples of such nucleic acid include nucleic acids used for so-called gene therapy, and the like.

The particle size of the lipid nanoparticle encapsulating a nucleic acid is not particularly limited, and is preferably nm to 500 nm, more preferably 30 nm to 300 nm. The particle size can be measured by using a particle size distribution measuring device such as Zetasizer Nano (Malvern) or the like. The particle size of the lipid nanoparticle encapsulating a nucleic acid can be appropriately adjusted by the production method thereof.

The surface charge (zeta potential) of the lipid nanoparticles encapsulating a nucleic acid is not particularly limited and preferably −15 to +15 mV, more preferably −10 to +10 mV. In conventional transgene, particles with positively charged surfaces have been mainly used. This is useful as a method for promoting electrostatic interactions with heparin sulfate on the negatively-charged cell surface to enhance uptake into cells. However, the positive surface potential may suppress (a) nucleic acid release from the carrier due to the interaction with a nucleic acid to be delivered in the cell, or (b) protein synthesis due to the interaction between mRNA and a nucleic acid to be delivered. This problem can be solved by adjusting the surface potential (zeta potential) to fall within the above-mentioned range. The surface potential (zeta potential) can be measured using a zeta potential measuring apparatus such as Zetasizer Nano or the like. The surface potential (zeta potential) of the lipid nanoparticles can be adjusted by the composition of the constituent components of the lipid nanoparticles.

By administering the lipid nanoparticles encapsulating nucleic acid of the present invention to a subject, the lipid nanoparticles reach and contact brain tissues, and the nucleic acid encapsulated in the lipid nanoparticles is delivered to the brain tissues in vivo. The subject to which the lipid nanoparticles can be administered is not particularly limited and, for example, mammals (e.g., human, monkey, mouse, rat, hamster, bovine, etc.), birds (e.g., chicken, ostrich, etc.), amphibia (e.g., frog etc.), fishes (e.g., zebrafish, medaka (Oryzias latipes), etc.), and the like can be mentioned. The subject of administration of the lipid nanoparticles is preferably human or other mammal.

The administration method of the lipid nanoparticles encapsulating nucleic acid to a subject is not particularly limited as long as the lipid nanoparticles can deliver nucleic acid to brain tissues, and an administration method known per se (e.g., oral administration, parenteral administration (e.g., transnasal administration, intravenous administration, intramuscular administration, topical administration, transdermal administration, subcutaneous administration, intraperitoneal administration, spray, etc.), etc.) can be appropriately selected. As the administration method, transnasal administration is preferred. The dose of the lipid nanoparticles can be appropriately selected in consideration of the kind of the subject of administration, administration method, and the like.

The lipid nanoparticles of the present invention may be used as they are, or mixed with a pharmaceutically acceptable carrier and can be produced as an oral agent (e.g., tablet, capsule agent, etc.) or a parenteral agent (e.g., nasal preparation, injection, inhalant, etc.), preferably a parenteral agent (more preferably, nasal preparation).

As the pharmaceutically acceptable carrier, those conventionally used as formulation materials are used. For example, in solid preparations, excipient, lubricant, binder, disintegrant, and the like are used, and in liquid preparations, solvent, solubilizing agent, suspending agent, isotonicity agent, buffering agent, soothing agent, and the like are used. Where necessary, formulation additives such as antiseptic, antioxidant, colorant, sweetening agent, and the like can also be used.

For example, in the case of nasal preparations, they are used in the form of nasal drops or sprays.

EXAMPLE

The Examples of the present invention are explained in further detail in the following, but the present invention is not limited in any way by the Examples.

In the following Examples and the like, ionic lipid (1) is shown by the name listed in the aforementioned Table. The abbreviations used in the following Examples and the like each mean the following.

Chol: cholesterol

DDW: deionized distilled water

DEPC: 1,2-dierucoyl-sn-glycero-3-phosphocholine

DiR: 1,1'-dioctadecyl-3,3,3',3'-tetramethylindotricarbocyanine iodide

DMG-PEG2000: 1,2-dimyristoyl-rac-glycerol, methoxypolyethylene glycol (number average molecular weight (Mn) of PEG: 2000)

DMG-PEG5000: 1,2-dimyristoyl-rac-glycerol, methoxypolyethylene glycol (number average molecular weight (Mn) of PEG: 5000) DOPC: 1,2-dioleoyl-sn-glycero-3-phosphocholine EPC: egg phosphatidylcholine MES: 2-morpholinoethanesulfonic acid PBS: phosphate buffered saline POPC: 1-palmitoyl-2-oleoyl-sn-glycero-3-phosphocholine SOPC: 1-stearoyl-2-oleoyl-sn-glycero-3-phosphocholine

Example 1: Preparation of Lipid Nanoparticles (LNP)

As lipids, SS—OP, DOPC, and Chol, and DMG-PEG5000 or DMG-PEG2000 (Comparative Example) were used. The molar ratio of SS—OP:DOPC:Chol used was 52.5:7.5:40, and 3 mol % of DMG-PEG5000 or DMG-PEG2000 was used with respect to the total of SS—OP, DOPC, and Chol. For particle labeling, 0.5 mol % of fluorescent dye DiR with respect to the total of SS—OP, DOPC, and Chol was added to an ethanol solution of the lipid.

An acidic malate buffer (20 mM, pH 3.0) (3750 μL) containing NaCl at a final concentration of 30 mM and an ethanol solution (1350 μL) of lipid were respectively weighed into a syringe. Using NanoAssmblr (registered trademark) ultra-high-speed nanomedicine production device (manufactured by Precision NanoSystems), LNP was prepared under the conditions of addition rate of acidic buffer solution: 3 mL/min, addition rate of ethanol solution of lipid: 1 mL/min, and syringe holder temperature: 25° C., and recovered into a 15 mL tube. MES buffer (pH 6.5) (3000 μL) was added to the 15 mL tube, the obtained mixture was transferred to Amicon Ultra 15, and concentrated to about 1500 μL by ultrafiltration under centrifugation conditions (25° C., 1000 g, 5 min). The obtained concentrate was diluted with MES buffer (pH 6.5) to 15 mL, and concentrated again to about 1500 μL by ultrafiltration under centrifugation conditions (25° C., 1000 g, 5 min). The obtained concentrate was diluted with PBS to 15 mL, and concentrated to about 1500 μL by ultrafiltration under centrifugation conditions (25° C., 1000 g, 5 min). The obtained concentrate was diluted with DDW to 15 mL, and concentrated to about 250 μL by ultrafiltration under centrifugation conditions (25° C., 1000 g, 5 min), which operation was performed two times. The obtained concentrate was transferred to Amicon Ultra 4, diluted with DDW to 4 mL, and again concentrated to about 100 μL by ultrafiltration under centrifugation conditions (25° C., 1000 g, 5 min). The obtained concentrate was diluted with DDW to a lipid concentration of 40 mM to obtain a dispersion containing LNP.

Experimental Example 1: Evaluation of Brain Migration of LNP by In Vivo Administration Three types of mixed anesthesia (100 μL/20 g mouse) was administered intraperitoneally to a mouse. Thirty minutes after the administration of the three types of mixed anesthesia, a dispersion containing LNP was administered at 5 μL/20 g mouse (total 10 μL/20 g mouse) to the left and right nasal cavities of the mouse at 3-minute intervals using a 10 μL pipette. At this time, the LHB method (administration method in a posture with head tilted back) and the administration method in a supine position (conventional method) were performed as methods for administering the dispersion containing LNP.

One hour after administration of the dispersion containing LNP, Antisedan (100 μL/20 g mouse) was intraperitoneally administered to the mouse, and the mouse was returned to a cage. Three hours after administration of Antisedan, the head of the mouse was excised and placed on ice. After 5 minutes, the entire brain was removed using dissection scissors. After removal of the brain, imaging was performed using IVIS Lumina II (Caliper) (measurement conditions: Imaging Mode: Fluorescent, Exposure Time: 10 sec, Binning: Medium, F/Stop: 2, Lamp Level: High, Excitation Filter: 745 nm, Emission Filter: ICG). As a result, in all administration methods, a tendency toward better migration of LNP to the brain was observed when DMG-PEG5000 was used than when DMG-PEG2000 was used. Particularly, when LNP using DMG-PEG5000 was administered by the LHB method, a tendency toward better migration into the brain was observed (FIG. 1). In FIG. 1, "DMG2k conventional method" and "DMG5k conventional method" respectively show the results of conventional methods using DMG-PEG2000 and DMG-PEG5000. In FIG. 1, "DMG2k LHB method" and "DMG2k LHB method" respectively show the results of LHB methods using DMG-PEG2000 and DMG-PEG5000.

Example 2: Preparation of Various LNPs with Different Molar Ratios of Ionic Lipid (1) and Phospholipid As lipids, SS—OP, DOPC, Chol, and DMG-PEG5000 were used. The molar ratio of SS—OP:DOPC:Chol used was "52.5:7.5:40", "45:15:40", or "30:30:40", and 3 mol % of DMG-PEG5000 was used with respect to the total of SS—OP, DOPC, and Chol. As comparison target, lipid nanoparticles containing egg phosphatidylcholine (EPC) instead of DOPC and SS—OP were used. Sample using EPC was EPC/Chol=70/30 and contained 3 mol % of DMG-PEG5000 with respect to the total of EPC and Chol. For particle labeling, 0.5 mol % of fluorescent dye DiR with respect to the total of SS—OP, DOPC, and Chol, or the total of EPC and Chol was added to the ethanol solution of lipid.

An acidic malate buffer (20 mM, pH 3.0) (2100 μL) containing NaCl at a final concentration of 30 mM and an ethanol solution (800 μL) of lipid were respectively weighed into a syringe. Using NanoAssmblr (registered trademark) ultra-high-speed nanomedicine production device (manufactured by Precision NanoSystems), 4 kinds of LNP were prepared under the conditions of addition rate of acidic buffer solution: 3 mL/min, addition rate of ethanol solution of lipid: 1 mL/min, and syringe holder temperature: 25° C., and each recovered into 15 mL tubes. MES buffer (pH 6.5) (3000 μL) was added to the 15 mL tube, the obtained mixture was transferred to Amicon Ultra 15, and concentrated to about 1500 μL by ultrafiltration under centrifugation conditions (25° C., 1000 g, 5 min). The obtained concentrate was diluted with MES buffer (pH 6.5) to 15 mL, and concentrated again to about 1500 μL by ultrafiltration under centrifugation conditions (25° C., 1000 g, 5 min). The obtained concentrate was diluted with PBS to 15 mL, and concentrated to about 1500 μL by ultrafiltration under centrifugation conditions (25° C., 1000 g, 5 min). The obtained concentrate was diluted with DDW to 15 mL, and concentrated to about 250 μL by ultrafiltration under centrifugation conditions (25° C., 1000 g, 5 min), which operation was performed two times. The obtained concentrate was transferred to Amicon Ultra 4, diluted with DDW to 4 mL, and again concentrated to about 50 μL by ultrafiltration under centrifugation conditions (25° C., 1000 g, 5 min). The obtained concentrate was diluted with DDW to a lipid concentration of 40 mM to obtain each dispersion containing LNP. The obtained dispersion was used in the following Experimental Example 2.

Experimental Example 2: Effect of Composition Ratio of Phospholipid on Brain Migration of LNP by In Vivo Administration Three types of mixed anesthesia (100 μL/20 g mouse) was administered intraperitoneally to a mouse, and the mouse was set on a particle administration table for LHB method. Thirty minutes after the administration of the three types of mixed anesthesia, a dispersion containing LNP was administered at 5 μL/20 g mouse (total 10 μL/20 g mouse) to the left and right nasal cavities of the mouse at 3-minute intervals using a 10 μL pipette.

Figure 2:
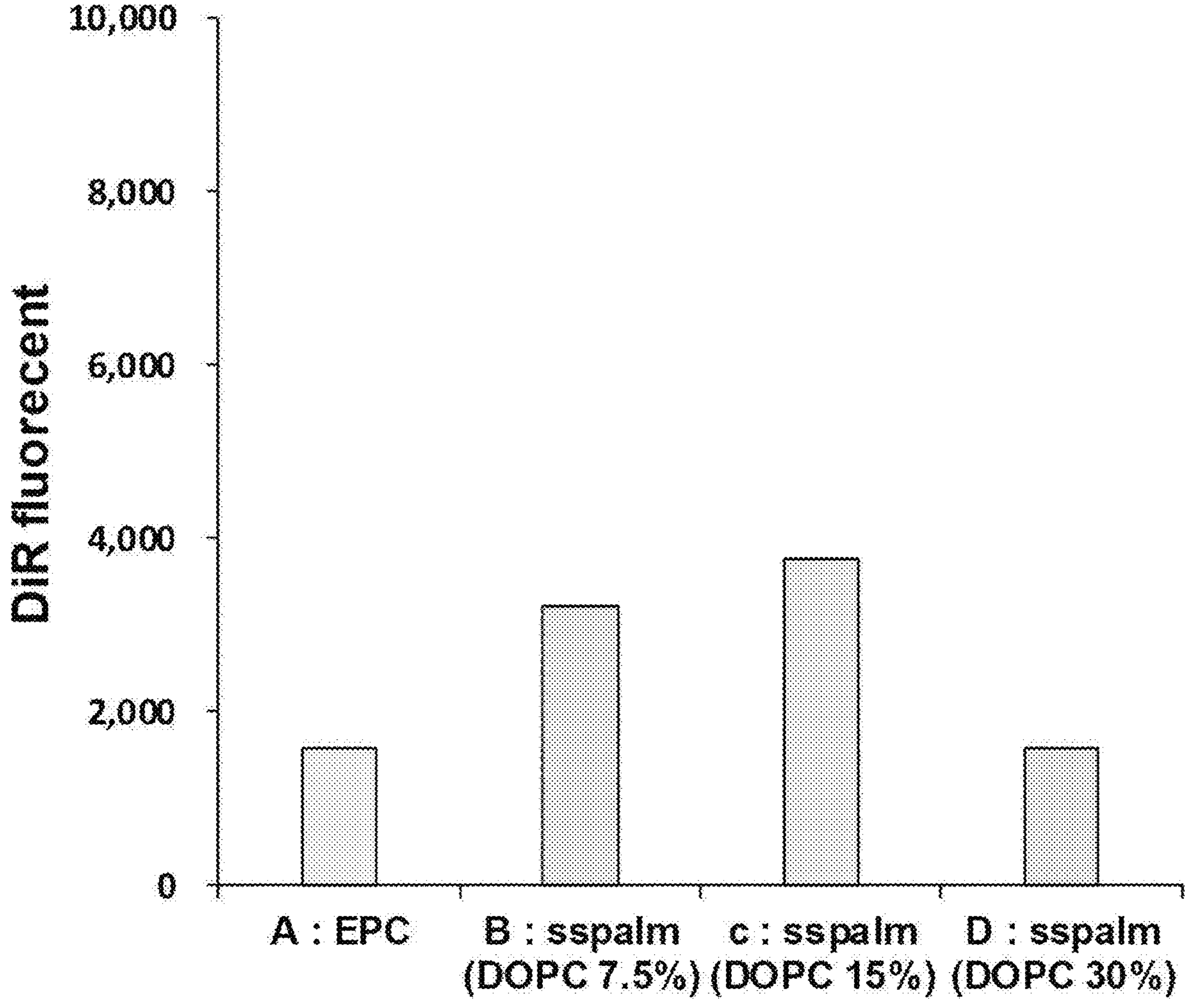
FIG. 2 is a diagram showing the effect of the composition ratio of the phospholipid (DOPC) on the brain migration of LNP during in vivo administration.

One hour after administration of the dispersion containing LNP, Antisedan (100 μL/20 g mouse) was intraperitoneally administered to the mouse, and the mouse was returned to a cage. Three hours after the administration, the head of the mouse was excised and placed on ice. After 5 minutes, the entire brain was removed using dissection scissors. After removal of the brain, imaging was performed using IVIS Lumina II (Caliper) (measurement conditions: Imaging Mode: Fluorescent, Exposure Time: 10 sec, Binning: Medium, F/Stop: 2, Lamp Level: High, Excitation Filter: 745 nm, Emission Filter: ICG). As a result, it was considered that DOPC 7.5 to 15% (SS—OP:DOPC:Chol=52.5 to 45:7.5 to 15:40), preferably 15%, is the composition ratio that facilitates migration into the brain (FIG. 2).

Example 3: Preparation of Various LNPs with Different Phospholipids

As lipids, SS—OP, phospholipid (DOPC, SOPC, POPC, DPPC, or DEPC), Chol, and DMG-PEG5000 were used. The molar ratio of SS—OP:phospholipid:Chol used was 45:15:40, and 3 mol % of DMG-PEG5000 was used with respect to the total of SS—OP, phospholipid, and Chol. For particle labeling, 0.5 mol % of fluorescent dye DiR with respect to the total of SS—OP, phospholipid, and Chol was added to an ethanol solution of the lipid.

An acidic malate buffer (20 mM, pH 3.0) (2100 μL) containing NaCl at a final concentration of 30 mM and an ethanol solution (800 μL) of lipid were respectively weighed into a syringe. Using NanoAssmblr (registered trademark) ultra-high-speed nanomedicine production device (manufactured by Precision NanoSystems), 5 kinds of LNP were prepared under the conditions of addition rate of acidic buffer solution: 3 mL/min, addition rate of ethanol solution of lipid: 1 mL/min, and syringe holder temperature: 25° C., and each recovered into 15 mL tubes. MES buffer (pH 6.5) (3000 μL) was added to the 15 mL tube, the obtained mixture was transferred to Amicon Ultra 15, and concentrated to about 1500 μL by ultrafiltration under centrifugation conditions (25° C., 1000 g, 5 min). The obtained concentrate was diluted with MES buffer (pH 6.5) to 15 mL, and concentrated again to about 1500 μL by ultrafiltration under centrifugation conditions (25° C., 1000 g, 5 min). The obtained concentrate was diluted with PBS to 15 mL, and concentrated to about 1500 μL by ultrafiltration under centrifugation conditions (25° C., 1000 g, 5 min). The obtained concentrate was diluted with DDW to 15 mL, and concentrated to about 250 μL by ultrafiltration under centrifugation conditions (25° C., 1000 g, 5 min), which operation was performed two times. The obtained concentrate was transferred to Amicon Ultra 4, diluted with DDW to 4 mL, and again concentrated to about 50 μL by ultrafiltration under centrifugation conditions (25° C., 1000 g, 5 min). The obtained concentrate was diluted with DDW to a lipid concentration of 40 mM to obtain each dispersion containing LNP. The obtained dispersion was used in the following Experimental Example 3.

Experimental Example 3: Effect of Kind of Phospholipid on Brain Migration of LNP by In Vivo Administration Three types of mixed anesthesia (100 μL/20 g mouse) was administered intraperitoneally to a mouse, and the mouse was set on a particle administration table for LHB method.

Thirty minutes after the administration of the three types of mixed anesthesia, a dispersion containing LNP was administered at 5 μL/20 g mouse (total 10 μL/20 g mouse) to the left and right nasal cavities of the mouse at 3-minute intervals using a 10 μL pipette.

Figure 3:
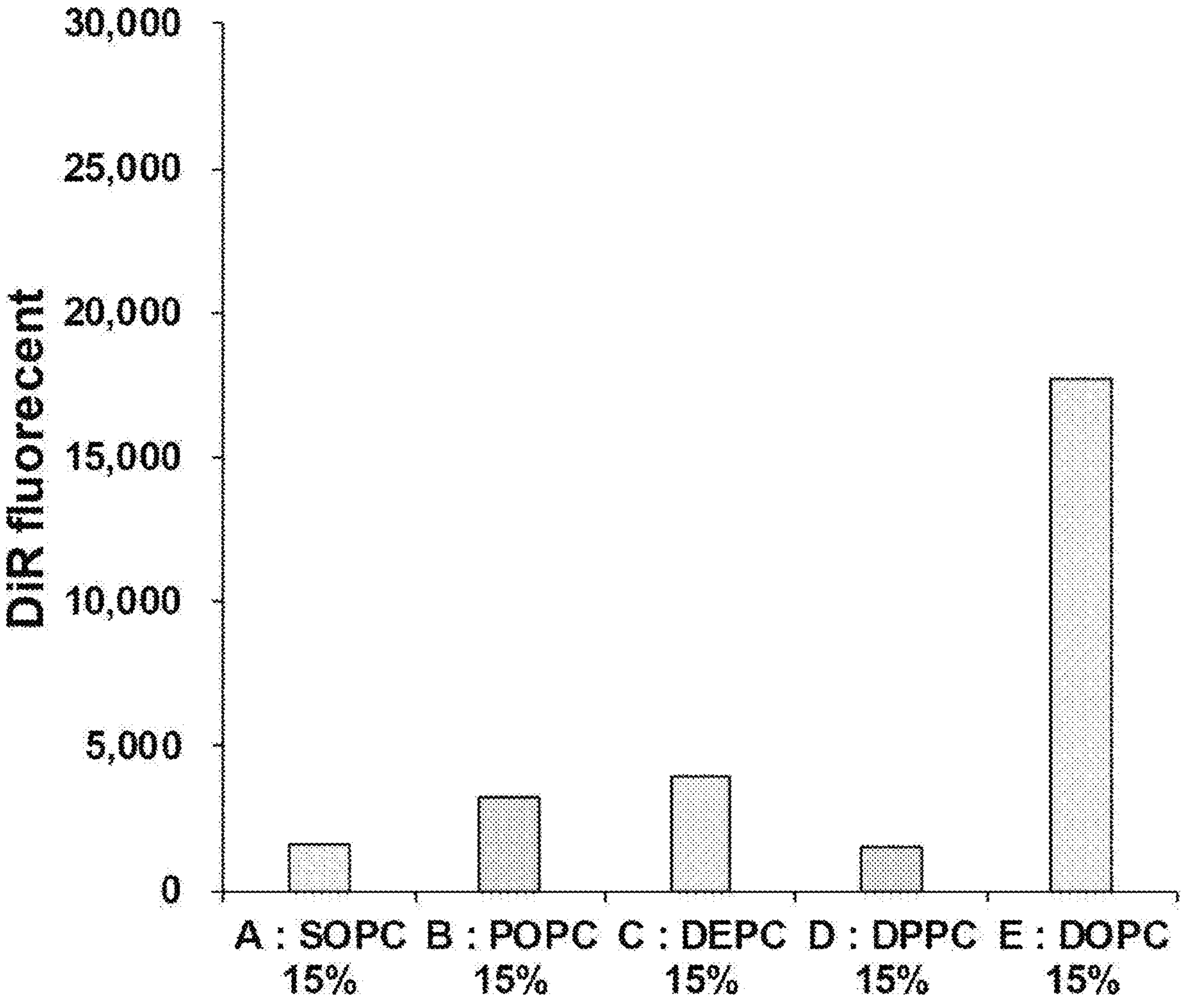
FIG. 3 is a diagram showing the effect of the kind of the phospholipid on the brain migration of LNP during in vivo administration.

One hour after administration of the dispersion containing LNP, Antisedan (100 μL/20 g mouse) was intraperitoneally administered to the mouse, and the mouse was returned to a cage. Three hours after the administration, the head of the mouse was excised and placed on ice. After 5 minutes, the entire brain was removed using dissection scissors. After removal of the brain, imaging was performed using IVIS Lumina II (Caliper) (measurement conditions: Imaging Mode: Fluorescent, Exposure Time: 10 sec, Binning: Medium, F/Stop: 2, Lamp Level: High, Excitation Filter: 745 nm, Emission Filter: ICG). As a result, it was considered that DOPC is the lipid that facilitates migration into the brain (FIG. 3).

Example 4: Preparation of Various LNPs with Different Molar Ratios of Ionic Lipid (1) and Cholesterol As lipids, SS—OP, DOPC, Chol, and DMG-PEG5000 were used. The molar ratio of SS—OP:DOPC:Chol used was "85:15:0", "65:15:20", "45:15:40", or "25:15:60", and 3 mol % of DMG-PEG5000 was used with respect to the total of SS—OP, DOPC, and Chol.

An acidic malate buffer (20 mM, pH 3.0) (2100 μL) containing mRNA encoding luciferase (CleanCap (registered trademark) FLuc mRNA—(L-7602)) at a final concentration of 0.0067 μg/μL and NaCl at a final concentration of 30 mM and an ethanol solution (800 μL) of lipid were respectively weighed into a syringe. Using NanoAssmblr (registered trademark) ultra-high-speed nanomedicine production device (manufactured by Precision NanoSystems), 4 kinds of LNP were prepared under the conditions of addition rate of acidic buffer solution: 3 mL/min, addition rate of ethanol solution of lipid: 1 mL/min, and syringe holder temperature: 25° C., and each recovered into 15 mL tubes. MES buffer (pH 6.5) (3000 μL) was added to the 15 mL tube, the obtained mixture was transferred to Amicon Ultra 15, and concentrated to about 1500 μL by ultrafiltration under centrifugation conditions (25° C., 1000 g, 5 min). The obtained concentrate was diluted with MES buffer (pH 6.5) to 15 mL, and concentrated again to about 1500 μL by ultrafiltration under centrifugation conditions (25° C., 1000 g, 5 min). The obtained concentrate was diluted with PBS to 15 mL, and concentrated to about 1500 μL by ultrafiltration under centrifugation conditions (25° C., 1000 g, 5 min). The obtained concentrate was diluted with DDW to 15 mL, and concentrated to about 250 μL by ultrafiltration under centrifugation conditions (25° C., 1000 g, 5 min), which operation was performed two times. The obtained concentrate was transferred to Amicon Ultra 4, diluted with DDW to 4 mL, and again concentrated to about 50 μL under centrifugation conditions (25° C., 1000 g, 5 min). The obtained concentrate was diluted with DDW to a lipid concentration of 40 mM to obtain each dispersion containing LNP. The obtained dispersion was used in the following Experimental Example 4.

Experimental Example 4: Effect of Composition Ratio of Cholesterol on Brain Migration of LNP by In Vivo Administration Three types of mixed anesthesia (100 μL/20 g mouse) was administered intraperitoneally to a mouse, and the mouse was set on a particle administration table for LHB method. Thirty minutes after the administration of the three types of mixed anesthesia, a dispersion containing LNP was administered at 5 μL/20 g mouse (total 10 μL/20 g mouse) to the left and right nasal cavities of the mouse at 3-minute intervals using a 10 μL pipette.

Figure 4:
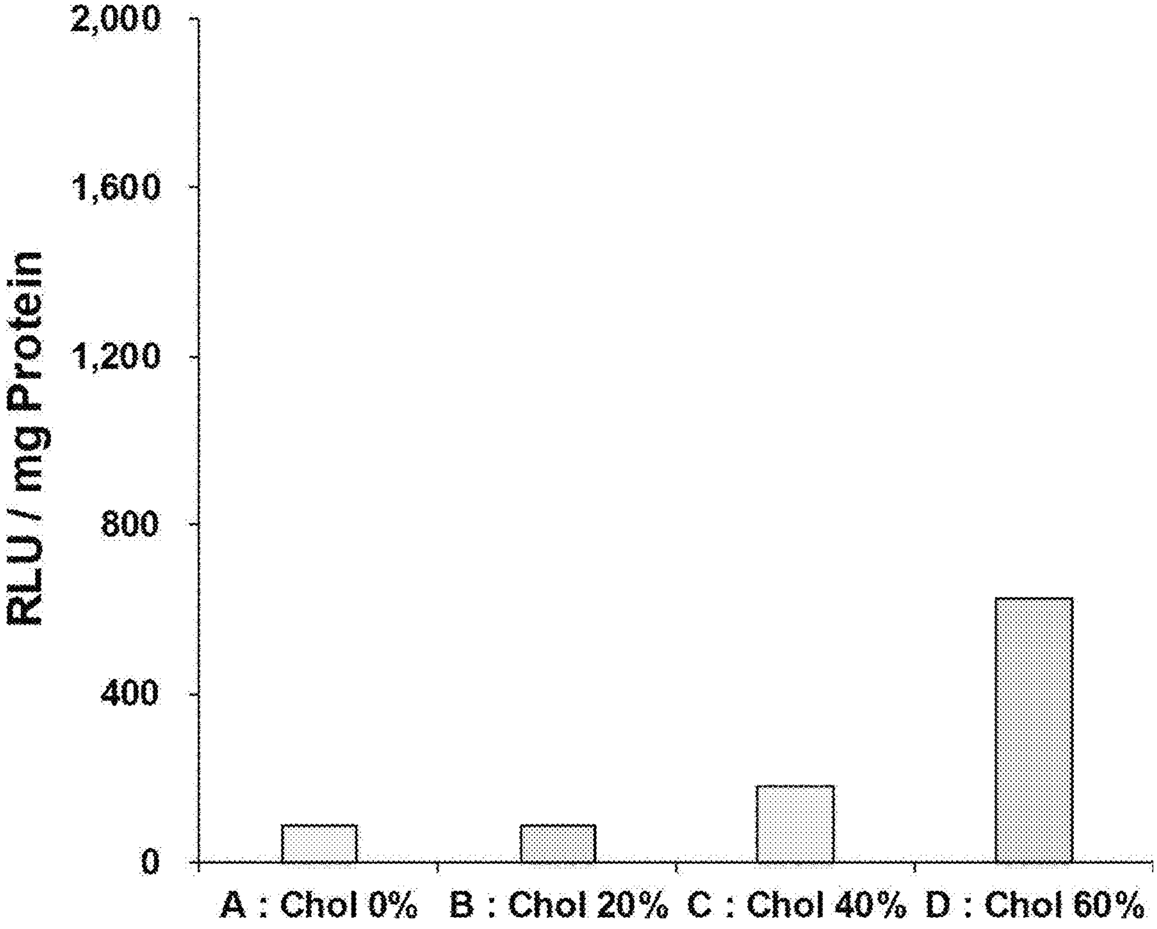
FIG. 4 is a diagram showing the effect of the composition ratio of cholesterol on the brain migration of LNP during in vivo administration.

One hour after administration of the dispersion containing LNP, Antisedan (100 μL/20 g mouse) was intraperitoneally administered to the mouse, and the mouse was returned to a cage. Eighteen hours after the administration, the head of the mouse was excised and placed on ice. After 5 minutes, the brain was removed using dissection scissors, placed in a crushing tube, and frozen with liquid nitrogen. In vivo Lysis Buffer (800 μL) was added to the crush tube and homogenized twice under the conditions of 4800 rpm and 30 seconds. The supernatant was recovered and centrifuged under the conditions of 13000 rpm, 4° C., and 10 min. Furthermore, the supernatant was recovered, luciferin (50 μL) was added to the supernatant (20 μL), and the luminescence was measured with a luminometer. As a result, it was considered that Chol 60% (SS—OP:DOPC:Chol=25:15:60) is the composition suitable for intracerebral protein expression (FIG. 4).

Example 5: Preparation of mRNA-Encapsulating LNP with Optimized Lipid Composition As lipids, SS—OP, DOPC, Chol, and DMG-PEG5000 were used, and an ethanol solution of lipid was prepared at a lipid composition assumed from the above-mentioned Experimental Examples to be most superior in the brain migration (molar ratio of SS—OP:DOPC:Chol was 25:15:60, and 3 mol % of DMG-PEG5000 was used with respect to the total of SS—OP, DOPC, and Chol). For particle labeling, 0.5 mol % of fluorescent dye DiR with respect to the total of SS—OP, DOPC, and Chol was added to an ethanol solution of the lipid.

An acidic malate buffer (20 mM, pH 3.0) containing mRNA encoding luciferase (CleanCap (registered trademark) FLuc mRNA—(L-7602)) at a final concentration of 0.0067 μg/pL and NaCl at a final concentration of 30 mM was weighed into a syringe by 2100 μL (number of administration 2), 3750 μL (number of administration 4), or 7200 μL (number of administration 8), and an ethanol solution of lipid was weighed into a syringe by 800 μL (number of administration 2), 1350 μL (number of administration 4), or 2500 μL (number of administration 8). Using NanoAssmblr (registered trademark) ultra-high-speed nanomedicine production device (manufactured by Precision NanoSystems), LNP was prepared under the conditions of addition rate of acidic buffer solution: 3 mL/min, addition rate of ethanol solution of lipid: 1 mL/min, and syringe holder temperature: 25° C., and recovered into a 15 mL tube. MES buffer (pH 6.5) (3000 μL) was added to the 15 mL tube, the obtained mixture was transferred to Amicon Ultra 15, and concentrated to about 1500 μL by ultrafiltration under centrifugation conditions (25° C., 1000 g, 5 min). The obtained concentrate was diluted with MES buffer (pH 6.5) to 15 mL, and concentrated again to about 1500 μL by ultrafiltration under centrifugation conditions (25° C., 1000 g, 5 min). The obtained concentrate was diluted with PBS to 15 mL, and concentrated to about 1500 μL by ultrafiltration under centrifugation conditions (25° C., 1000 g, 5 min). The obtained concentrate was diluted with DDW to 15 mL, and concentrated to about 250 μL by ultrafiltration under centrifugation conditions (25° C., 1000 g, 5 min), which operation was performed two times. The obtained concentrate was transferred to Amicon Ultra 4, diluted with DDW to 4 mL, and again concentrated by ultrafiltration under centrifugation conditions (25° C., 1000 g, 5 min) to about 50 μL (number of administration 2), 100 μL (number of administration 4), or 200 μL (number of administration 8). The obtained concentrate was diluted with DDW to a lipid concentration of 40 mM to obtain a dispersion containing LNP. The obtained dispersion was used in the following Experimental Example 5.

Experimental Example 5: Effect of Number of Administration on Brain Migration of LNP by In Vivo Administration Three types of mixed anesthesia (100 μL/20 g mouse) was administered intraperitoneally to a mouse, and the mouse was set on a particle administration table for LHB method. Thirty minutes after the administration of the three types of mixed anesthesia, a dispersion containing LNP was administered at 5 μL/20 g mouse (total 10 μL/20 g mouse) (number of administration 2 (one administration set)), 20 μL/20 g mouse (number of administration 4 (two administration sets)), or 40 μL/20 g mouse (number of administration 8 (four administration sets)) to the left and right nasal cavities of the mouse at 3-minute intervals using a 10 μL pipette.

Figures 1, 5:
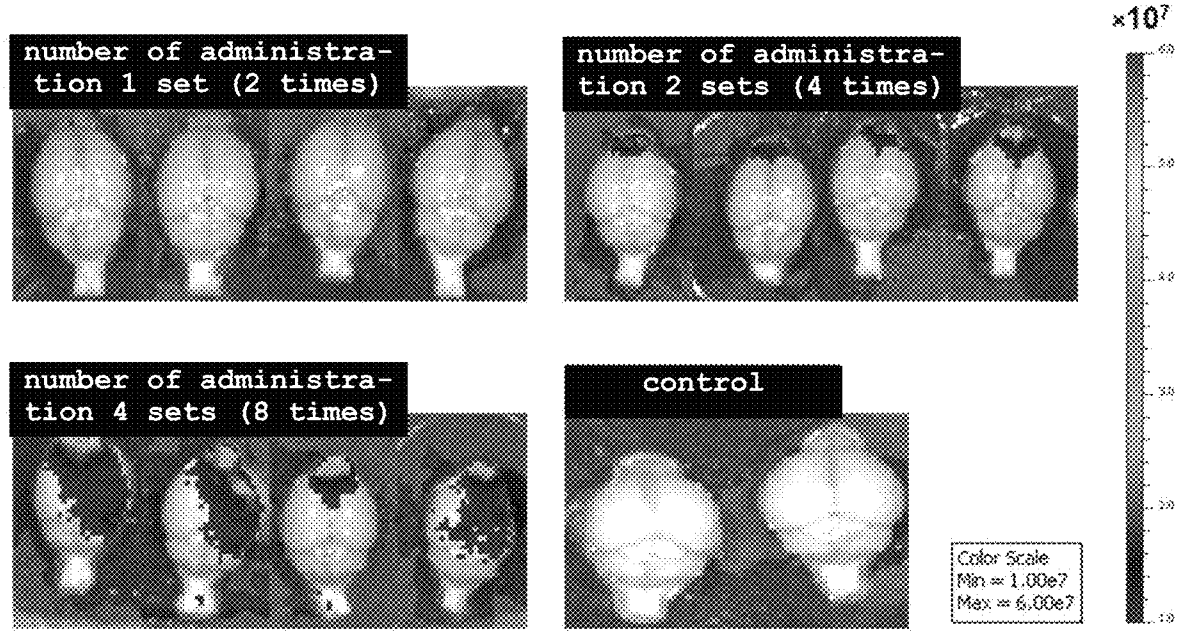
Figures 2, 5:
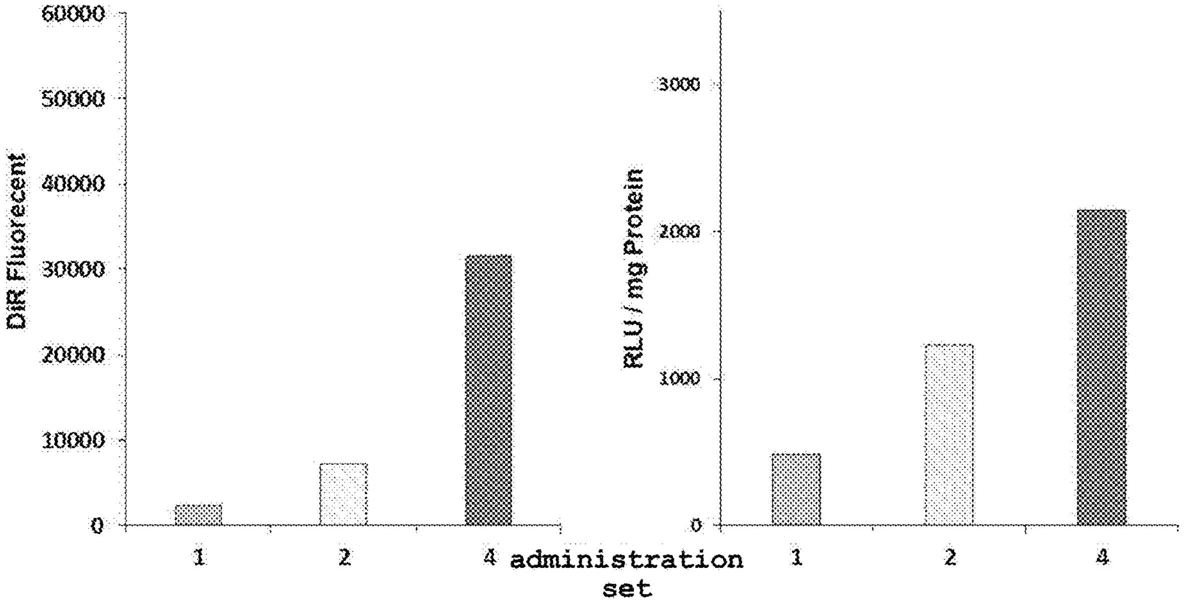

One hour after administration of the dispersion containing LNP, Antisedan (100 μL/20 g mouse) was intraperitoneally administered to the mouse, and the mouse was returned to a cage. Eighteen hours after the administration, the head of the mouse was excised and placed on ice. After 5 minutes, the entire brain was removed using dissection scissors. After removal of the brain, imaging was performed using IVIS Lumina II (Caliper) (measurement conditions: Imaging Mode: Fluorescent, Exposure Time: 10 sec, Binning: Medium, F/Stop: 2, Lamp Level: High, Excitation Filter: 745 nm, Emission Filter: ICG). Then, the brain was placed in a crushing tube, and frozen with liquid nitrogen. In vivo Lysis Buffer (800 μL) was added to the crush tube and homogenized twice at 4800 rpm for seconds. The supernatant was recovered and centrifuged under the conditions of 13000 rpm, 4° C., and 10 min. Furthermore, the supernatant was recovered, luciferin (50 μL) was added to the supernatant (20 μL), and the luminescence was measured with a luminometer. As a result, dosage-dependent brain migration (FIG. 5-1 and FIG. 5-2, left) and intracerebral expression of luciferase (FIG. 5-2, right) were observed.

Example 6: Preparation of mRNA-Encapsulating LNP with Lipid Composition Optimized for Brain Migration Similar to Example 5, an ethanol solution of lipid was prepared at a lipid composition assumed from the above-mentioned Experimental Examples to be most superior in the brain migration (molar ratio of SS—OP:DOPC:Chol was 25:15:60, and 3 mol % of DMG-PEG5000 was used with respect to the total of SS—OP, DOPC, and Chol).

For comparison, as lipids, SS—OP, DOPC, Chol, and DMG-PEG2000 were used, and an ethanol solution of lipid was prepared at a lipid composition known to be superior in liver migration (molar ratio of SS—OP:DOPC:Chol was 52.5:7.5:40, and 3 mol % of DMG-PEG2000 was used with respect to the total of SS—OP, DOPC, and Chol).

For particle labeling, 0.5 mol % of fluorescent dye DiR with respect to the total of SS—OP, DOPC, and Chol was added to each ethanol solution of the lipid.

An acidic malate buffer (20 mM, pH 3.0) (9750 μL) containing mRNA encoding luciferase (CleanCap (registered trademark) FLuc mRNA—(L-7602)) at a final concentration of 0.0067 μg/μL and NaCl at a final concentration of 30 mM and an ethanol solution (3000 μL) of lipid were respectively weighed into a syringe. Using NanoAssmblr (registered trademark) ultra-high-speed nanomedicine production device (manufactured by Precision NanoSystems), 2 kinds of LNP were prepared under the conditions of addition rate of acidic buffer solution: 3 mL/min, addition rate of ethanol solution of lipid: 1 mL/min, and syringe holder temperature: 25° C., and each recovered into 15 mL tubes. MES buffer (pH 6.5) (3000 μL) was added to the 15 mL tube, the obtained mixture was transferred to Amicon Ultra 15, and concentrated to about 1500 μL by ultrafiltration under centrifugation conditions (25° C., 1000 g, 5 min). The obtained concentrate was diluted with MES buffer (pH 6.5) to 15 mL, and concentrated again to about 1500 μL by ultrafiltration under centrifugation conditions (25° C., 1000 g, 5 min). The obtained concentrate was diluted with PBS to 15 mL, and concentrated to about 1500 μL by ultrafiltration under centrifugation conditions (25° C., 1000 g, 5 min). The obtained concentrate was diluted with DDW to 15 mL, and concentrated to about 250 μL by ultrafiltration under centrifugation conditions (25° C., 1000 g, 5 min), which operation was performed two times. The obtained concentrate was transferred to Amicon Ultra 4, diluted with DDW to 4 mL, and again concentrated to about 250 μL by ultrafiltration under centrifugation conditions (25° C., 1000 g, 5 min). The obtained concentrate was diluted with DDW to a lipid concentration of 40 mM to obtain each dispersion containing LNP. The obtained dispersion was used in the following Experimental Example 6.

Experimental Example 6: Verification of Optimization of Conditions for Brain Migration of LNP by In Vivo Administration Three types of mixed anesthesia (100 μL/20 g mouse) was administered intraperitoneally to a mouse, and the mouse was set on a particle administration table for LHB method. Thirty minutes after the administration of the three types of mixed anesthesia, a dispersion containing LNP was administered at 5 μL/20 g mouse (total 40 μL/20 g mouse) (number of administration 8 (four administration sets)) to the left and right nasal cavities of the mouse at 3-minute intervals using a 10 μL pipette.

Figures 1, 6:
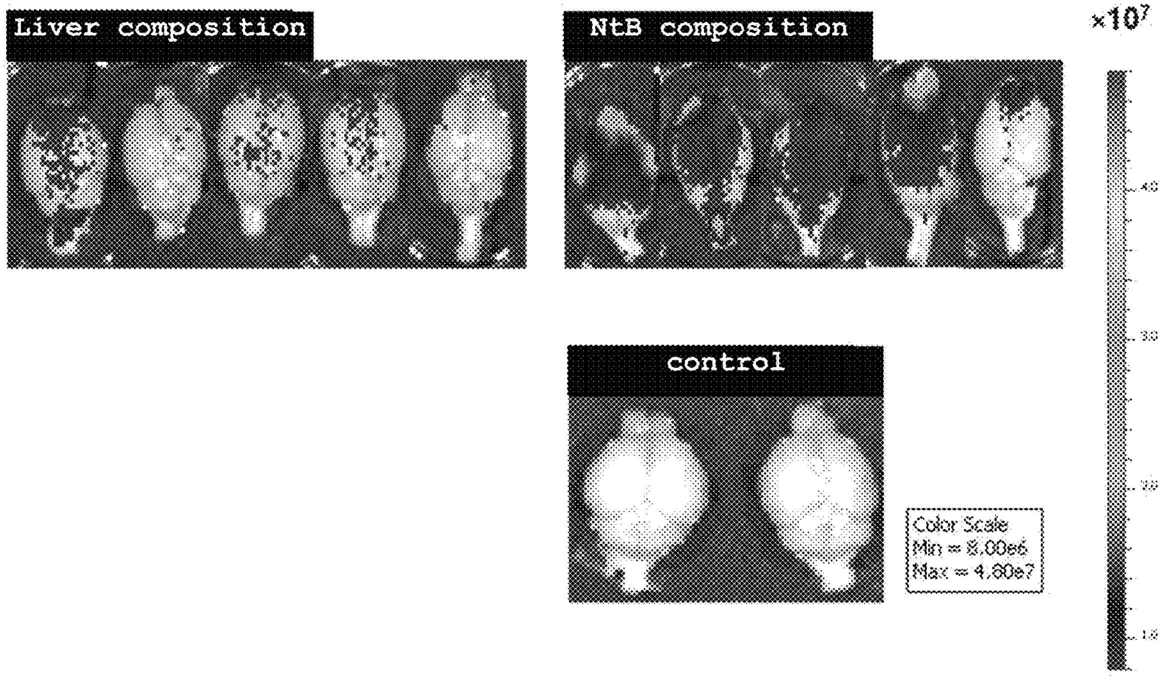
Figures 2, 6:
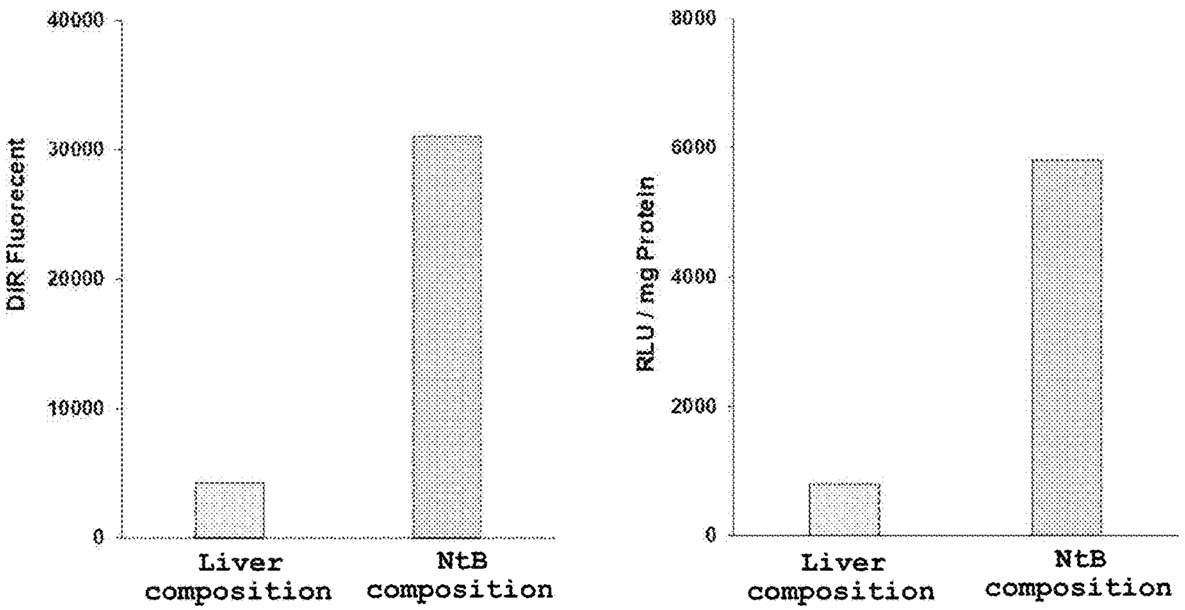

One hour after administration of the dispersion containing LNP, Antisedan (100 μL/20 g mouse) was intraperitoneally administered to the mouse, and the mouse was returned to a cage. Eighteen hours after the administration, the head of the mouse was excised and placed on ice. After 5 minutes, the entire brain was removed using dissection scissors. After removal of the brain, imaging was performed using IVIS Lumina II (Caliper) (measurement conditions: Imaging Mode: Fluorescent, Exposure Time: 10 sec, Binning: Medium, F/Stop: 2, Lamp Level: High, Excitation Filter: 745 nm, Emission Filter: ICG). Then, the brain was placed in a crushing tube, and frozen with liquid nitrogen. In vivo Lysis Buffer (800 μL) was added to the crush tube and homogenized twice under the conditions of 4800 rpm for 30 seconds. The supernatant was recovered and centrifuged under the conditions of 13000 rpm, 4° C., and 10 min. Furthermore, the supernatant was recovered, luciferin (50 μL) was added to the supernatant (20 μL), and the luminescence was measured with a luminometer. As a result, compared with the composition (Liver composition) and dosage for liver migration, the composition (NtB composition) and dosage selected for brain migration were confirmed to be significantly high in the brain migration (FIG. 6-1 and FIG. 6-2, left) and intracerebral expression level of luciferase (FIG. 6-2, right), and it was considered that the conditions for LNP for brain migration could be optimized.

INDUSTRIAL APPLICABILITY

The lipid nanoparticles of the present invention are useful for delivering nucleic acids to brain tissues.

This application is based on a patent application No. 2021-161237 filed in Japan, the contents of which are incorporated in full herein.

The invention claimed is:

1. A lipid nanoparticle used for delivering a nucleic acid to a brain tissue, comprising (1)

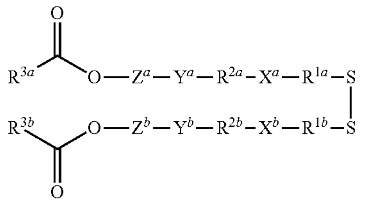

wherein $R^{1a}$ and $R^{1b}$ are each independently an alkylene group having 1 to 6 carbon atoms, $X^a$ and $X^b$ are each independently an acyclic alkyl tertiary amino group having 1 to 6 carbon atoms and one tertiary amino group, or a cyclic alkylene tertiary amino group having 2 to 5 carbon atoms and 1 to 2 tertiary amino groups, $R^{2a}$ and $R^{2b}$ are each independently an alkylene group or an oxydialkylene group each having not more than 8 carbon atoms, $Y^a$ and $Y^b$ are each independently an ester bond, an amide bond, a carbamate bond, an ether bond or a urea bond, $Z^a$ and $Z^b$ are each independently a divalent group derived from an aromatic compound having 3 to 16 carbon atoms and at least one aromatic ring, and optionally having a hetero atom, and $R^{3a}$ and $R^{3b}$ are each independently a residue derived from a reaction product of a liposoluble vitamin having a hydroxyl group, and succinic anhydride or glutaric anhydride, or a residue derived from a reaction product of a sterol derivative having a hydroxyl group, and succinic anhydride or glutaric anhydride, or an aliphatic hydrocarbon group having 12 to 22 carbon atoms, (ii) phospholipid, (iii) cholesterol, and (iv) a dimyristoylglycerol PEG represented by the formula (2):

$$CH_2(OR^6)—CH(OR^7)—CH_2(OR^8) \quad (2)$$

wherein two of $R^6$, $R^7$, and $R^8$ are myristoyl groups, and the remaining one is an alkyl group having 1 to 6 carbon atoms connected via a polyethylene glycol chain with a number average molecular weight of 4,000 to 6,000, wherein an amount of the dimyristoylglycerol PEG represented by the formula (2) is 1 to 6 mol % with respect to the total of the ionic lipid represented by the formula (1), the phospholipid, and the cholesterol.

2. The lipid nanoparticle according to claim 1, wherein lipids constituting the lipid nanoparticle consist of the ionic lipid represented by the formula (1), the phospholipid, the cholesterol, and the dimyristoylglycerol PEG represented by the formula (2).

3. The lipid nanoparticle according to claim 2, wherein the ionic lipid represented by the formula (1) is an ionic lipid represented by the following formula:

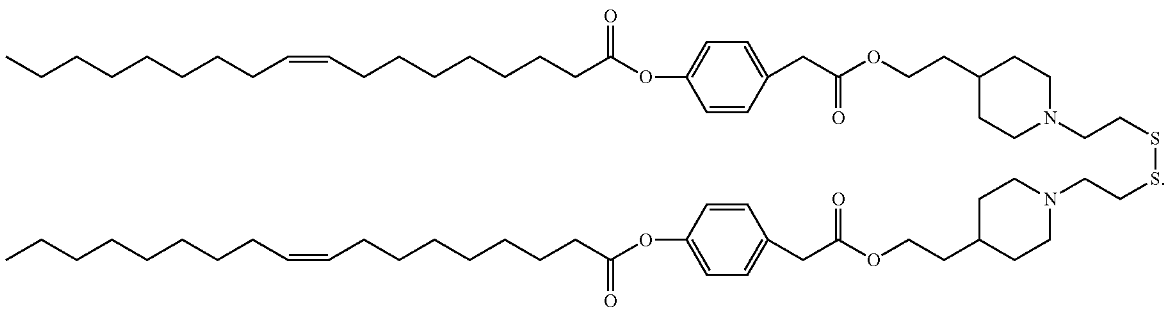 [SMILES: CCCCCCCC/C=C\CCCCCCCC(=O)Oc1ccc(CC(=O)OCCC2CCN(CCSSCCN3CCC(CCOC(=O)Cc4ccc(OC(=O)CCCCCCC/C=C\CCCCCCCC)cc4)CC3)CC2)cc1]

4. The lipid nanoparticle according to claim 3, wherein the phospholipid is 1,2-dioleoyl-sn-glycero-3-phosphocholine.

5. The lipid nanoparticle according to claim 4, wherein an amount of the ionic lipid represented by the formula (1) is 15 to 70 mol %, an amount of the phospholipid is 5 to 25 mol %, and an amount of the cholesterol is 25 to 80 mol %, with respect to the total of the ionic lipid represented by the formula (1), the phospholipid, and the cholesterol.

6. The lipid nanoparticle according to claim 2, wherein the phospholipid is 1,2-dioleoyl-sn-glycero-3-phosphocholine.

7. The lipid nanoparticle according to claim 6, wherein an amount of the ionic lipid represented by the formula (1) is 15 to 70 mol %, an amount of the phospholipid is 5 to 25 mol %, and an amount of the cholesterol is 25 to 80 mol %, with respect to the total of the ionic lipid represented by the formula (1), the phospholipid, and the cholesterol.

8. The lipid nanoparticle according to claim 2, wherein an amount of the ionic lipid represented by the formula (1) is 15 to 70 mol %, an amount of the phospholipid is 5 to 25 mol %, and an amount of the cholesterol is 25 to 80 mol %, with respect to the total of the ionic lipid represented by the formula (1), the phospholipid, and the cholesterol.

9. The lipid nanoparticle according to claim 1, wherein the ionic lipid represented by the formula (1) is an ionic lipid represented by the following formula:

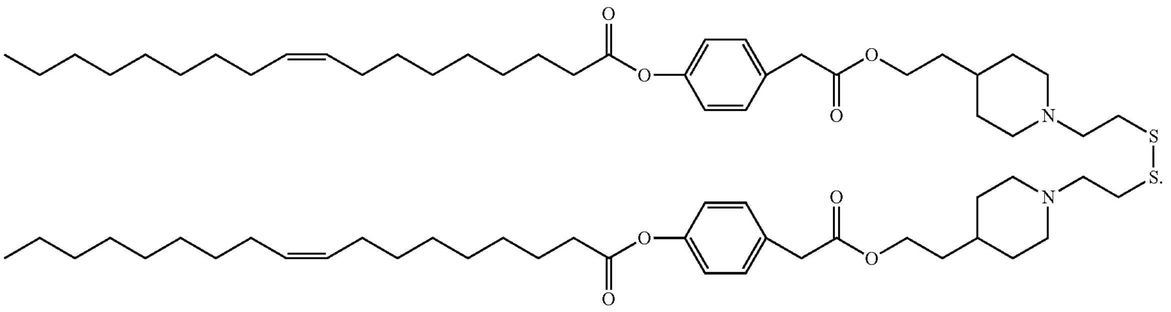 [SMILES: CCCCCCCC/C=C\CCCCCCCC(=O)Oc1ccc(CC(=O)OCCC2CCN(CCSSCCN3CCC(CCOC(=O)Cc4ccc(OC(=O)CCCCCCC/C=C\CCCCCCCC)cc4)CC3)CC2)cc1]

10. The lipid nanoparticle according to claim 1, wherein the phospholipid is 1,2-dioleoyl-sn-glycero-3-phosphocholine.

11. The lipid nanoparticle according to claim 1, wherein an amount of the ionic lipid represented by the formula (1) is 15 to 70 mol %, an amount of the phospholipid is 5 to 25 mol %, and an amount of the cholesterol is 25 to 80 mol %, with respect to the total of the ionic lipid represented by the formula (1), the phospholipid, and the cholesterol.

12. A method for delivering a nucleic acid to a brain tissue, comprising transnasally administering the lipid nanoparticle according to claim 1 that encapsulates the nucleic acid to a subject.

13. A method for delivering a nucleic acid to a brain tissue, comprising transnasally administering the lipid nanoparticle according to claim 2 that encapsulates the nucleic acid to a subject.

14. A method for delivering a nucleic acid to a brain tissue, comprising transnasally administering the lipid nanoparticle according to claim 9 that encapsulates the nucleic acid to a subject.

15. A method for delivering a nucleic acid to a brain tissue, comprising transnasally administering the lipid nanoparticle according to claim 10 that encapsulates the nucleic acid to a subject.

16. A method for delivering a nucleic acid to a brain tissue, comprising transnasally administering the lipid nanoparticle according to claim 11 that encapsulates the nucleic acid to a subject.

17. A method for delivering a nucleic acid to a brain tissue, comprising transnasally administering the lipid nanoparticle according to claim 3 that encapsulates the nucleic acid to a subject.

18. A method for delivering a nucleic acid to a brain tissue, comprising transnasally administering the lipid nanoparticle according to claim 4 that encapsulates the nucleic acid to a subject.

19. A method for delivering a nucleic acid to a brain tissue, comprising transnasally administering the lipid nanoparticle according to claim 5 that encapsulates the nucleic acid to a subject.

20. A method for delivering a nucleic acid to a brain tissue, comprising transnasally administering the lipid nanoparticle according to claim 6 that encapsulates the nucleic acid to a subject.

* * * * *